(12) United States Patent
Abuljadayel

(10) Patent No.: US 7,112,440 B2
(45) Date of Patent: *Sep. 26, 2006

(54) METHOD OF INCREASING THE RELATIVE NUMBER OF CD45 LOW CELLS IN A CELL POPULATION

(75) Inventor: Ilham Abuljadayel, London (GB)

(73) Assignee: Ghazi Jaswinder Dhoot, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 09/742,520

(22) Filed: Dec. 20, 2000

(65) Prior Publication Data

US 2001/0024826 A1    Sep. 27, 2001

Related U.S. Application Data

(62) Division of application No. 09/521,700, filed on Mar. 9, 2000, now abandoned, which is a division of application No. 08/594,164, filed on Jan. 31, 1996, now Pat. No. 6,090,625.

(30) Foreign Application Priority Data

Feb. 2, 1995    (GB)    ................................. 9502022.8

(51) Int. Cl.
    C12N 5/08    (2006.01)
(52) U.S. Cl. .................... 435/372; 435/7.21; 435/7.23; 435/7.24; 435/377
(58) Field of Classification Search ................ 435/7.1, 435/7.21–7.24, 34, 372, 372.2, 377; 436/501
    See application file for complete search history.

(56) References Cited

U.S. PATENT DOCUMENTS

| | | | |
|---|---|---|---|
| 4,528,265 A | 7/1985 | Becker | |
| 5,004,681 A | 4/1991 | Boyse et al. | |
| 5,843,780 A | 12/1998 | Thomson | |
| 6,200,806 B1 | 3/2001 | Thomson | |
| 6,227,202 B1 | 5/2001 | Matapurkar | ................. 128/898 |

OTHER PUBLICATIONS

Cruse, Illustrated Dictionary of Immunology, CRC Press, p. 37, 1995.*
Pettersen et al, (Journal of Immunology, 1998, vol. 160, pp. 4343-4352).*
Genestier et al (Blood, 1997, vol. 90, pp. 3629-3639).*
Genestier et al (Blood, 1997, vol. 90, pp. 726-735).*
Woodle et al, (Journal of Immunology, 1997, vol. 158, pp. 2156-2164).*
Vidovic and Toral (Cancer Letter, 1998, vol. 128, pp. 127-135).*
Thibeault et al (Cellular Immunology, 1999, vol. 192, pp. 79-85).*
Betro et al (Journal of Immunology, 2000, vol. 164, pp. 2379-2385).*
Abstract of Tawara et al (Blood, 2001, vol. 98, pp. 250-B.*
Cruse et al, Illustrated Dictionary of Immunology, CRC Press, Inc., 1995, pp. 35 and 173.*

Boral et al. Blood Preservation in Transfusion Medicine, pp. 938-846, in Henry, J., ed., Clinical Diagnosis and Management by Laboratory Methods. 18th ed., W.B. Saunders Company, Philadelphia, 1991.
Uriel, J., "Cancer, Retrodifferentiation, and the Myth of Faust". Cancer Research 36, 4269-4275, 1976. Sato et al., Blood, 82(12):3600-3609, Dec. 1993.
Nelson et al., "Basic Examination of Blood", pp. 553-603 in Clinical Diagnosis & Management By Laboratory Methods, Henry, J.B. ed., W. B. Saunders Company, Philadelphia, 1991.
Nelson et al., "Hematopoiesis", pp. 604-626, in Clinical Diagnosis & Management By Laboratory Methods, Henry, J.B., ed., W.B. Saunders Company, Philadelphia, 1991.
Ogawa et al., "Renewal and Committment to Differentiation of Hemopoietic Stem Cells (An Interpretive Review)", Blood, vol. 61, No. 5, pp. 823-829, May 1983.
The Molecular Control of Cell Division. Differentiation Committment and Maturation in Haemopeietic Cells, vol. 339, pp. 27-30, May 1989.
Jordan et al., "Cellular and Development Properties of Fetal Hematopoietic Stem Cells", pp. 953-963, Cell, vol. 61, Jun. 1990.
Spangrude et al., "Purification and Characterization of Mouse Hematopoietic Stem Cells", Science, vol. 241, pp. 58-62, Jul. 1988.
Orlie et al., What Defines a Pluripotent Hematopoietic Stem Cell (PHSC): Would the Real PHSC Please Stand Up?, Blood, vol. 84, No. 12, pp. 3991-3994, Dec. 1994.
Moore et al., "Clinical Implications of Positive and Negative Hematopoietic Stem Cell Regulators", Blood, vol. 78, pp. 1-19, Jul. 1991.
Moorehead, P.S., "Human Blood Leukocytes", pp. 58-61, in Tissue Culture, ed. Kruse et al., Academic Press, New York, 1973.
Stedman's Medical Dictionary, 24th ed., p. 1352, Williams & Wilkens, Baltimore, 1982.
Hass, R., "Retrodifferentiation—an alternative biological pathway in human leukemia cells", European Journal of Cell Biology, 58:1-11, 1992.
Altomonte, M., et al., "Cross-Linking of HLA Class II Antigens Modulates the Release of Tumor Necrosis Factor-alpha by the EBV-B Lymphoblastoid Cell Line JY," The Journal of Immunology (151(10):5115-5122.
Cambier, J.C., et al., "Molecular Mechanisms of Transmembrane Signaling in B Lymphocytes," in Ann Rev Imm. (1987) 5:175-199.
Cambier, J.C., et al., "Ia-Mediated Signal Transduction Leads to Proliferation of Primed B Lymphocytes," J Exp Med (1989) 170:877-886.
Clement, I., T., et al., "Antibodies Reactive with Class II Antigens Encoded for by the Major Histocompatibility Complex inhibit human B Cell Activation," The Journal of Immunology (1986) 136(7):2375-2381.

(Continued)

Primary Examiner—David Saunders
(74) Attorney, Agent, or Firm—Frommer Lawrence & Haug LLP; Thomas J. Kowalski

(57) ABSTRACT

A method of increasing the relative number of CD45 low cells in a cell population is described. The method comprises contacting a more committed cell with an agent that causes the more committed cell to retrodifferentiate into an undifferentiated cell, which undifferentiated cell is a CD45 low cell.

14 Claims, 6 Drawing Sheets

OTHER PUBLICATIONS

Deeg, H.J., et al., "Major histocompatibility complex class II molecules, hemopoiesis and the marrow microenvironment," Bone Marrow Transplantation (1993) 12:425-430.

Ghaderi, A.A., et al., "Cross-linking of a sequential epitope within the .alpha.-chain of HLA-DR DP molecules suppressing B lymphocyte growth and inducing homotypic cell aggregation," Immunology Letters (1994) 39:113-119.

Hajeer, A.H., et al., "Antibodies to major histocompatibility complex class II inhibit proliferation, but increase production of soluble CD23 in lymphoblastoid B-cell lines," Immunology (1993) 80:593-597.

Huss, R., et al., "Major Histocompatibility Complex Class II Expression is Required for Posttransplant Immunological but not for Hemopoietic Reconstitution in Mice," Transplantation (1994) 58(12):1366-1371.

Huss, R., et al., "Differentiation of canine bone marrow cells with hemopoietic characteristics from an adherent stromal cell precursor," Proc Natl Acad Sci USA (1995) 92:748-752.

Mooney, N., et al., "HLA Class-II Antigen-Mediated Induction of a Proliferative Response to Anti-IgM in Human B Lymphocytes," Int J Cancer (1991) Supplement 6:30-33.

Mooney, N.A., et al., "Bacterial Superantigen Signaling via HLA Class II on Human B Lymphocytes," Molecular Immunology (1994) 31(9):675-681.

Morio, T., et al., "Engagement of MHC class II molecules by staphylococcal superantigens activates src-type protein tyrosine kinases," Eur J Immunol (1994) 24:651-658.

Naitoh, K., et al., "Signal Transmission through MHC Class II Molecules in a Human B Lymphoid Progenitor Cell Line: Different Signaling Pathways Depending on the Maturational Stages of B Cells," Microbiol Immunol (1994) 38(12):967-976.

Newell, M.K., et al., "Ligation of major histocompatibility complex class II molecules mediates apoptotic cell death in resting B lymphocytes." Proc Natl Acad Sci USA (1993) 90(Nov):10459-10463.

Perl, A., et al., "Rearrangement of the T-Cell Receptor Alpha. Beta and Gamma Chain Genes in Chronic Lymphocytic Leukemia," Leukemia Research (1990) 14(2):131-137.

Scholl, P.R., et al., "MHC class II signaling in B-cell activation," Immunology Today (1994) 15(9):418-422.

Takahama, Y., et al., "Disparate functions of I-A and I-E molecules on B cells as evidenced by the inhibition with anti-I-A and anti-I-E antibodies of polyclonal B cell activation," Eur J Immunol (1989) 19:2227-2235.

Truman, J-P., et al., "Lymphocyte programmed cell death is mediated via HLA class II DR," International Immunology (1994) 6(6):887-896.

Wade, W.F., et al., "Structural compartmentalization of MHC class II signaling function," Immunology Today (1993) 14(11):539-546.

J. Uriel: Cancer Research 36, 4269-4275: Nov. 1976: Cancer, Retrodifferentiation, and the Myth of Faust.

M. Fukuda: Cancer Research, 41: 4621-4628: Nov. 1981; Tumor-producing Phorbol Diester-induced specific changes in Cell Surface Glycoprotein Profile of K562 Human Leukemie Cells.

N.J. Curtin, et al.; Br. J. Cancer (1983) 48:495-505; Enzymic retrodifferentiation during hepatocarcinogenesis and liver regeneration in rats in vivo.

E. Chastre, et al.: FEBS Letters: Sep. 1985; vol. 188, No. 2; Vasoactive intestinal peptide receptor activity and specificity during enterocyte-like differentiation and retrodifferentiation of the human colonic cancerous subclone HT29-18.

R. Hass, et al.:Cell Growth & Differentiation; vol. 2, Nov. 1991; pp. 541-548; Protein Kinase C Activation and Protooncogene Expression in Differentiation/Retrodifferentiation of Human U-937 Leukemia Cells.

M. Kobayashi, et al.; Pergamon Leukemia Research, vol. 18, No. 12; pp. 929-933; 1994; Establishment of a retrodifferentiated cell line from a single differentiated rat myclomonocytic leukemia cell:possible roles of retrodifferentiation in relapses of leukemia after diff-inducing therapy.

Goro Eguchi and Ryuji Kodama, "Transdifferentiation" Cell Biology 1993, 5:1023-1028.

Margaret H. Baron, "Reversibility of the differentiated state in somatic cells" Cell Biology 1993, 5:1050-1056.

Abuljadayel, I.S., "Induction of Stem Cell-Like Plasticity in Mononuclear Cells Derived from Unmobilised Adult Human Peripheral Blood," Current Medical Research and Opinion, 19(5): 355-375, 2003.

Abuljadayel, I.S. et al., "SCID Repopulating Cells Derived from Unmobilised Adult Human Peripheral Blood," Current Medical Research and Opinion, 20(1): 87-100, 2004.

Scripps Research Institute Press Release: "Regenerative Chemical Turns Muscle Cells into Stem Cells, Say Scientists at the Scripps Research Institute", Dec. 22, 2003.

Wickenhauser et al. CD34+ human hemopoietic progenitor cells of the bone marrow differ from those of the peripheral blood: an immunocytochemical and morphometric study. Acta Haematol 1995;93(2-4):83-90.

Trischmann et al. Measurement of CD34+ cells in bone marrow by flow cytometry. J Hematother 1993 Fall;2(3):305-13.

Abrahamsen et al. Flow cytometric assessment of peripheral blood contamination and proliferative activity of human bone marrow populations. Cytometry Jan. 1, 1995;19(1):77-85.

Festin et al. Multicolor flow cytometric analysis of the CD45 antigen provides improved lymphoid cell discrimination in bone marrow and tissue biopsies. J Immunol Methods Dec. 28, 1994;177(1-2):215-24.

Shah et al. Flow cytometric analysis of human bone marrow, IV. Differential quantitative expression of T-200 common leukocyte antigen during normal hemopoiesis. J Immunol Mar. 15, 1988;140(6):1861-7.

Dick et al. Flow cytometric identification of a minority population of MHC class II positive cells in the normal rat retina distinct from CD45lowCD11b/c_CD4low parenchymal microglia. Br J Ophthalmol Sep. 1995;79(9):834-40.

Gane et al. Flow cytometric evaluation of human basophils. Cytometry 1993;14(3):344-8.

Paramithiotis et al. High levels of CD45 are coordinatedly expressed with CD4 and CD8 on avian thymocytes. J Immunol Dec. 1, 1991;147(11):3710-7.

Pilarski et al. Beta 1 integrin (CD29) expression on human postnatal T cell subsets defined by selective CD45 isoform expression. J Immunol Aug. 1, 1991;147(3):830-7.

Sedgwick et al. Isolation and direct characterization of resident microglial cells from the normal and inflamed central nervous system. Proc Natl Acad Sci USA Aug. 1991;88:7438-42.

Zhao et al. A human peripheral blood monocyte-derived subset acts as pluripotent stem cells; vol. 100: PNAS 2003; 2426-2431.

* cited by examiner

METHOD OF INCREASING THE RELATIVE NUMBER OF CD45 LOW CELLS IN A CELL POPULATION

RELATED APPLICATIONS

This application is divisional of U.S. patent application Ser. No. 09/521,700, filed Mar. 9, 2000 and now abandoned, which in turn is a Divisional of application Ser. No. 08/594,164, filed Jan. 31, 1996, now U.S. Pat. No. 6,090,625.

The present invention relates to a method of preparing an undifferentiated cell.

FIELD OF THE INVENTION

In particular, the present invention relates to a method of preparing an undifferentiated cell from a more committed cell.

In addition the present invention relates to the use of the undifferentiated cell of the present invention for the preparation of a new more committed cell—i.e. a recommitted cell.

The present invention also relates to the use of the undifferentiated cell of the present invention or the recommitted cell of the present invention to have an effect (directly or indirectly via the use of products obtained therefrom) on the immune system, such as the alleviation of symptoms associated with, or the partial or complete cure from, an immunological condition or disease.

BACKGROUND OF THE INVENTION

By way of introduction, differentiation is a process whereby structures and functions of cells are progressively committed to give rise to more specialised cells, such as the formation of T cells or B cells. Therefore, as the cells become more committed, they become more specialised.

In contrast, retro-differentiation is a process whereby structures and functions of cells are progressively changed to give rise to less specialised cells.

Undifferentiated cells are capable of multilineage differentiation—i.e. they are capable of differentiating into two or more types of specialised cells. A typical example of an undifferentiated cell is a stem cell.

In contrast, differentiated cells are incapable of multilineage differentiation. A typical example of a differentiated cell is a T cell.

There are many undifferentiated cells and differentiated cells found in vivo and the general art is replete with general teachings on them.

By way of example, reference may be made to inter alia Levitt and Mertelsman 1995 (Haematopoietic Stem Cells, published by Marcel Dekker Inc—especially pages 45–59) and Roitt et al (Immunology, 4th Edition, Eds. Roitt, Brostoff and Male 1996, Publ. Mosby—especially Chapter 10).

In short, however, examples of undifferentiated cells include lymphohaematopoietic progenitor cells (LPCs). LPCs include pluripotent stem cells (PSCs), lymphoid stem cells (LSCs) and myeloid stem cells (MSCs). LSCs and MSCs are each formed by the differentiation of PSCs. Hence, LSCs and MSCs are more committed than PSCs.

Examples of differentiated cells include T cells, B cells, eosinophils, basophils, neutrophils, megakaryocytes, monocytes, erythrocytes, granulocytes, mast cells, and lymphocytes.

T cells and B cells are formed by the differentiation of LSCs. Hence, T cells and B cells are more committed than LSCs.

Eosinophils, basophils, neutrophils, megakaryocytes, monocytes, erythrocytes, granulocytes, mast cells, NKs, and lymphocytes are formed by the differentiation of MSCs. Hence, each of these cells are more committed than MSCs.

Antigens are associated with undifferentiated and differentiated cells. The term "associated" here means the cells expressing or capable of expressing, or presenting or capable of being induced to present, or comprising, the respective antigen(s).

Most undifferentiated cells and differentiated cells comprise Major Histocompatability Complex (MHC) Class I antigens and/or Class II antigens. If these antigens are associated with those cells then they are called Class $I^+$ and/or Class $II^+$ cells.

Each specific antigen associated with an undifferentiated cell or a differentiated cell can act as a marker. Hence, different types of cells can be distinguished from each other on the basis of their associated particular antigen(s) or on the basis of a particular combination of associated antigens.

Examples of these marker antigens include the antigens CD34, CD19 and CD3. If these anigens are present then these particular cells are called $CD34^+$, $CD19^+$ and $CD3^+$ cells respectively. If these antigens are not present then these cells are called $CD34^-$, $CD19^-$ and $CD3^-$ cells respectively.

In more detail, PSCs are $CD34^+$ cells. LSCs are $DR^+$, $CD34^+$ and $TdT^-$ cells. MSCs are $CD34^+$, $DR^+$, $CD13^+$, $CD33^+$, $CD7^+$ and $TdT^+$ cells. B $CD19^+$, $CD21^+$, $CD22^+$ and $DR^+$ cells. T cells are $CD2^-$, $CD3^-$, or $CD8^+$ cells. Immature lymphocytes are $CD4^+$ and $CD8^+$ cells. Activated T cells are $DR^+$ cells. Natural killer cells (NKs) are $CD56^+$ and $CD16^+$ cells. T lymphocytes are $CD7^+$ cells. Leukocytes are $CD45^+$ cells. Granulocytes are $CD13^+$ and $CD33^-$ cells. Monocyte macrophage cells are $CD14^+$ and $DR^+$ cells.

Hence, by looking for the presence of the above-listed antigen markers it is possible to identify certain cell types (e.g. whether or not a cell is an undifferentiated cell or a differentiated cell) and the specialisation of that cell type (e.g. whether that cell is a T cell or a B cell).

The general concept of retrodifferentiation is not new. In fact, in 1976 Jose Uriel (Cancer Research 36, 4269–4275. November 1976) presented a review on this topic, in which he said:

"retrodifferentiation appears as a common adaptive process for the maintenance of cell integrity against deleterious agents of varied etiology (physical, chemical, and viral). While preserving the entire information encoded on its genome, cells undergoing retrodifferentiation lose morphological and functional complexity by virtue of a process of self-deletion of cytoplasmic structures and the transition to a more juvenile pattern of gene expression. This results in a progressive uniformization of originally distinct cell phenotypes and to a decrease of responsiveness to regulatory signals operational in adult cells. Retrodifferentiation is normally counterbalanced by a process of reontogeny that tends to restore the terminal phenotypes where the reversion started. This explains why retrodifferentiation remains invariably associated to cell regeneration and tissue repair."

Uriel (ibid) then went on to discuss cases of reported retrodifferentiation—such as the work of Gurdon relating to nuclei from gut epithelial cells of Xenopus tadpoles (Advances in Morphogenesis [1966] vol 4, pp 1–43. New York Academic Press, Eds Abercrombie and Bracher), and the work of Bresnick relating to regeneration of liver (Methods in Cancer Research [1971] vol 6, pp 347–391).

Uriel (ibid) also reported on work relating to isolated liver parenchymal cells for in vitro cultures. According to Uriel:

"Contrary to the results with fetal or neonatal hepatocytes, with hepatocytes from regenerating liver, or from established hepatomas, it has been difficult to obtain permanent class lines from resting adult hepatocytes."

Uriel (ibid) also reported on apparent retrodifferentiation in cancer, wherein he stated:

"the biochemical phenotypes of many tumours show analogous changes of reversion toward immaturity . . . during the preneoplastic phase of liver carcinogenesis, cells also retrodifferentiate."

More recent findings on retrodifferentiation include the work of Minoru Fukunda (Cancer Research [1981] vol 41, pp 4621–4628). Fukunda induced specific changes in the cell surface glycoprotein profile of K562 human leukaemic cells by use of the tumour-promoting phorbol ester, 12-O-tetradecanoyl-phorbol-13-acetate (TPA). According to Fukunda TPA appeared to induce the K562 human leukaemic cells into a retrodifferentiated stage.

Also, Hass et al (Cell Growth & Differentiation [1991] vol 2, pp 541–548) reported that long term culture of TPA-differentiated U-937 leukaemia cells in the absence of phorbol ester for 32–36 days resulted in a process of retrodifferentiation and that the retrodifferentiated cells detached from the substrate and reinitiated proliferation.

Another case of retrodifferentiation is the work of Curtin and Snell (Br. J. Cancer [1983] vol 48, pp 495–505]. These workers compared enzymatic changes occurring during diethylnitrosamine-induced hepatocarcinogenesis and liver regeneration after partial hepatectomy to normal liver differentiation. Theses workers found changes in enzyme activities during carcinogenesis that were similar to a stepwise reversal of differentiation. According to these workers, their results suggest that an underlying retrodifferentiation process is common to both the process of hepatocarcinogenesis and liver regeneration.

More recently, Chastre et al (FEBS Letters [1985] vol 188, number 2, pp 2810–2811] reported on the retrodifferentiation of the human colonic cancerous subclone HT29-18.

Even more recently, Kobayashi et al (Leukaemia Research [1994] vol 18, no. 12, pp 929–933) have reported on the establishment of a retrodifferentiated cell line (RD-1) from a single rat myelomonocyticleukemia cell which differentiated into a macrophage-like cell by treatment with lipopolysaccharide (LPS).

According to the current understanding, as borne out by the teachings found on page 911 of Molecular Biology of the Cell (pub. Garland Publishers Inc. 1983) and more recently Levitt and Mertelsman (ibid), a stem cell, such as a PSC, has the following four characteristics:

i. it is an undifferentiated cell—i.e. it is not terminally differentiated;
ii. it has the ability to divide without limit;
iii. it has the ability to give rise to differentiated progeny, such as the differentiated cells mentioned earlier; and
iv. when it divides each daughter has a choice: it can either remain as PSC like its parent or it can embark on a course leading irreversibly to terminal differentiation.

Note should be made of the last qualification, namely that according to the general teachings in the art once an undifferentiated cell has differentiated to a more committed cell it can not then retrodifferentiate. This understanding was even supported by the teachings of Uriel (ibid), Fukunda (ibid), Hass et al (ibid), Curtin and Snell (ibid), Chastre et al (ibid), and Kobayashi et al (ibid) as these workers retrodifferentiated certain types of differentiated cells but wherein those cells remained committed to the same lineage and they did not retrodifferentiate into undifferentiated cells.

SUMMARY OF THE INVENTION

Therefore, according to the state of the art before the present invention, it was believed that it was not possible to form undifferentiated cells, such as stem cells, from more committed cells. However, the present invention shows that this belief is inaccurate and that it is possible to form undifferentiated cells from more committed cells.

Thus, according to a first aspect of the present invention there is provided a method of preparing an undifferentiated cell, the method comprising contacting a more committed cell with an agent that causes the more committed cell to retrodifferentiate into an undifferentiated cell.

According to a second aspect of the present invention there is provided a method comprising contacting a more committed cell with an agent that causes the more committed cell to retrodifferentiate into an undifferentiated cell; and then committing the undifferentiated cell to a recommitted cell.

The term "recommitted cell" means a cell derived from the undifferentiated cell—i.e. a new more committed cell.

According to a third aspect of the present invention there is provided an undifferentiated cell produced according to the method of the present invention.

According to a fourth aspect of the present invention there is provided an undifferentiated cell produced according to the method of the present invention as or in the preparation of a medicament.

According to a fifth aspect of the present invention there is provided the use of an undifferentiated cell produced according to the method of the present invention in the manufacture of a medicament for the treatment of an immunological disorder or disease.

According to a sixth aspect of the present invention there is provided a recommitted cell produced according to the method of the present invention.

According to a seventh aspect of the present invention there is provided a recommitted cell produced according to the method of the present invention as or in the preparation of a medicament.

According to an eighth aspect of the present invention there is provided the use of a recommitted cell produced according to the method of of the present invention in the manufacture of a medicament for the treatment of an immunological disorder or disease.

According to a ninth aspect of the present invention there is provided a more committed cell having attached thereto an agent that can cause the more committed cell to retrodifferentiate into an undifferentiated cell.

According to a tenth aspect of the present invention there is provided a $CD19^+$ and $CD3^+$ cell.

Thus, in its broadest sense, the present invention is based on the highly surprising finding that it is possible to form an undifferentiated cell from a more committed cell.

The present invention is highly advantageous as it is now possible to prepare undifferentiated cells from more committed cells and then use those undifferentiated cells as, or to prepare, medicaments either in vitro or in vivo or combinations thereof for the treatments of disorders.

The present invention is also advantageous as it is possible to commit the undifferentiated cell prepared by retrodifferentiation to a recommitted cell, such as a new differentiated cell, with a view to correcting or removing the original more committed cell or for correcting or removing a product thereof.

Preferably, the more committed cell is capable of retrodifferentiating into an MHC Class I$^+$ and/or an MHC Class II$^+$ undifferentiated cell.

Preferably, the more committed cell is capable of retrodifferentiating into an undifferentiated cell comprising a stem cell antigen.

Preferably, the more committed cell is capable of retrodifferentiating into a CD34$^+$ undifferentiated cell.

Preferably, the more committed cell is capable of retrodifferentiating into a lymphohaematopoietic progenitor cell.

Preferably, the more committed cell is capable of retrodifferentiating into a pluripotent stem cell.

The undifferentiated cell may comprise any components that are concerned with antigen presentation, capture or recognition. Preferably, the undifferentiated cell is an MHC Class I$^+$ and/or an MHC Class II$^+$ cell.

Preferably, the undifferentiated cell comprises a stem cell antigen.

Preferably, the undifferentiated cell is a CD34$^+$ undifferentiated cell.

Preferably, the undifferentiated cell is a lymphohaematopoietic progenitor cell.

Preferably, the undifferentiated cell is a pluripotent stem cell.

The more committed cell may comprise any components that are concerned with antigen presentation, capture or recognition. Preferably, the more committed cell is an MHC Class I$^+$ and/or an MHC Class II$^+$ cell.

Preferably, the agent acts extracelluarly of the more committed cell.

Preferably, the more committed cell comprises a receptor that is operably engageable by the agent and wherein the agent operably engages the receptor.

Preferably, the receptor is a cell surface receptor.

Preferably, the receptor comprises an α-component and/or a β-component.

Preferably, the receptor comprises a β-chain having homologous regions.

Preferably, the receptor comprises at least the homologous regions of the β-chain of HLA-DR.

Preferably, the receptor comprises an α-chain having homologous regions.

Preferably, the receptor comprises at least the homologous regions of the α-chain of HLA-DR.

Preferably, the agent is an antibody to the receptor.

Preferably, the agent is a monoclonal antibody to the receptor.

Preferably, the agent is an antibody, preferably a monoclonal antibody, to the homologous regions of the β-chain of HLA-DR.

Preferably, the agent is an antibody, preferably a monoclonal antibody, to the homologous regions of the α-chain of HLA-DR.

Preferably, the agent is used in conjunction with a biological response modifier.

Preferably, the biological response modifier is an alkylating agent.

Preferably, the alkylating agent is or comprises cyclophosphoamide.

In one preferred embodiment, the more committed cell is a differentiated cell.

Preferably, the more committed cell is any one of a B cell or a T cell.

In an alternative preferred embodiment, the more committed cell is a more mature undifferentiated cell.

In one preferred embodiment, when the undifferentiated cell is committed to a recommitted cell the recommitted cell is of the same lineage as the more committed cell prior to retrodifferentiation.

In another preferred embodiment, when the undifferentiated cell is committed to a recommitted cell the recommitted cell is of a different lineage as the more committed cell prior to retrodifferentiation.

Preferably, the recommitted cell is any one of a B cell, a T cell or a granulocyte.

Preferably, the method is an in vitro method.

Preferably, the agent modulates MHC gene expression, preferably wherein the agent modulates MHC Class I$^+$ and/or MHC Class II$^+$ expression.

The agent operably engages the more committed cell in order to retrodifferentiate that cell into an undifferentiated cell. In this regard, the agent for the retrodifferentiation of the more committed cell into the undifferentiated cell may act in direct engagement or in indirect engagement with the more committed cell.

An example of direct engagement is when the more committed cell has at least one cell surface receptor on its cell surface, such as a β-chain having homologous regions (regions that are commonly found having the same or a similar sequence) such as those that may be found on B cells, and wherein the agent directly engages the cell surface receptor. Another example, is when the more committed cell has a cell surface receptor on its cell surface such as an α-chain having homologous regions such as those that may be found on T cells, and wherein the agent directly engages the cell surface receptor.

An example of indirect engagement is when the more committed cell has at least two cell surface receptors on its cell surface and engagement of the agent with one of the receptors affects the other receptor which then induces retrodifferentiation of the more committed cell.

The agent for the retrodifferentiation of the more committed cell into an undifferentiated cell may be a chemical compound or composition. Preferably, however, the agent is capable of engaging a cell surface receptor on the surface of the more committed cell. For example, preferred agents include any one or more of cyclic adenosine monophosphate (cAMP), a CD4 molecule, a CD8 molecule, a part or all of a T-cell receptor, a ligand (fixed or free), a peptide, a T-cell receptor (TCR), an antibody, a cross-reactive antibody, a monoclonal antibody, or a polyclonal antibody.

If the agent is an antibody, a cross-reactive antibody, a monoclonal antibody, or a polyclonal antibody, then preferably the agent is any one or more of an antibody, a cross-reactive antibody, a monoclonal antibody, or a polyclonal antibody to any one or more of: the β chain of a MHC class II antigen, the β chain of a MHC HLA-DR antigen, the α chain of a MHC class I or class II antigen, the α chain of HLA-DR antigen, the α and the β chain of MHC class II antigen or of a MHC class I antigen. An example of a suitable antibody is CR3/43 (supplied by Dako).

The more committed cell is any cell derived or derivable from an undifferentiated cell.

Thus, in one preferred emdodiment, the more committed cell is also an undifferentiated cell. By way of example therefore the undifferentiated cell can be a lymphoid stem cell or a myeloid stem cell, and the undifferentiated cell is a pluripotent stem cell.

In another preferred embodiment, the more committed cell is a differentiated cell, such as a CFC-T cell, a CFC-B cell, a CFC-Eosin cell, a CFC-Bas cell, a CFC-Bas cell, a CFC-GM cell, a CFC-MEG cell, a BFC-E cell, a CFC-E cell, a T cell, a B cell, an eosinophil, a basophil, a neutrophil, a monocyte, a megakaryocyte or an erythrocyte; and the undifferentiated cell is a myeloid stem cell, a lymphoid stem cell or a pluripotent stem cell.

If the more committed cell is a differentiated cell then preferably the differentiated cell is a B lymphocyte (activated or non-activated), a T lymphocyte (activated or non-activated), a cell from the macrophage monocyte lineage, a nucleated cell capable of expressing class I or class II antigens, a cell that can be induced to express class I or class II antigens or an enucleated cell (i.e. a cell that does not contain a nucleus—such as a red blood cell).

In alternative preferred embodiments, the differentiated cell is selected from any one of a group of cells comprising large granular lymphocytes, null lymphocytes and natural killer cells, each expressing the CD56 and/or CD16 cell surface receptors.

The differentiated cell may even be formed by the nucleation of an enucleated cell.

The agent may act intracellularly within the more committed cell. However, preferably, the agent acts extracellularly of the more committed cell.

In a preferred embodiment, agent operably engages a receptor present on the surface of the more committed cell—which receptor may be expressed by the more committed cell, such as a receptor that is capable of being expressed by the more committed cell.

Preferably, the receptor is a Class I or a Class II antigen of the major histocompatibility complex (MHC). In preferred embodiments the cell surface receptor is any one of: an HLA-DR receptor, a DM receptor, a DP receptor, a DQ receptor, an HLA-A receptor, an HLA-B receptor, an HLA-C receptor, an HLA-E receptor, an HLA-F receptor, or an HLA-G receptor.

In more preferred embodiments the cell surface receptor is an HLA-DR receptor.

Preferably the contacting step comprises the agent engaging with any one or more of the following: homologous regions of the α-chain of class I antigens, homologous regions of the α-chain of class II antigens, a CD4 cell surface receptor, a CD8 cell surface receptor, homologous regions of the β-chain of class II antigens in the presence of lymphocytes, homologous regions of the α-chain of class I antigens in the presence of lymphocytes, or homologous regions of the α-chain of class II antigens in the presence of lymphocytes.

Preferably the contacting step occurs in the presence of the biological response modifier.

Preferably the biological response modifier is any one or more of a modulator, such as an immunomodulator, a growth factor, a cytokine, a cell surface receptor, a hormone, a nucleic acid, a nucleotide sequence, an antigen or a peptide.

In a preferred embodiment of the present invention the undifferentiated cell is then committed into a recommitted cell, such as a differentiated cell.

The recommitted cell may be of the same lineage to the more committed cell from which the undifferentiated cell was derived.

Alternatively, the recommitted cell may be of a different lineage to the more committed cell from which the undifferentiated cell was derived.

In addition, the present invention also encompasses the method of the present invention for preparing an undifferentiated cell, wherein the method includes committing the undifferentiated cell into a recommitted cell and then fusing the recommitted cell to a myeloma. This allows the expression in vitro of large amounts of the desired product, such as an antibody or an antigen or a hormone etc.

Other aspects of the present invention include:

The use of any one of the agents of the present invention for preparing an undifferentiated cell from a more committed cell.

The use of an undifferentiated cell produced according to the method of the present invention for producing any one of a monoclonal or a polyclonal or a specific antibody from a B-lymphocyte or a T-lymphocyte; a cell from the macrophage monocyte lineage; a nucleated cell capable of expressing class I or class II antigens; a cell capable of being induced to express class I or class II antigens; an enucleated cell; a fragmented cell; or an apoptic cell.

The use of an undifferentiated cell produced according to the method of the present invention for producing effector T-lymphocytes from B-lymphocytes and/or vice versa.

The use of an undifferentiated cell produced according to the method of the present invention for producing any one or more of: a medicament, such as a medicament comprising or made from a B-lymphocyte, a T-lymphocyte, a cell from the macrophage monocyte lineage, a nucleated cell capable of expressing a class I or a class II antigen, a cell capable of being induced to express a class I or a class II antigen, or an enucleated cell.

The present invention also encompasses processes utilising the afore-mentioned uses and products or compositions prepared from such processes.

The present invention also encompasses a medicament comprising an undifferentiated cell according to the present invention or a product obtained therefrom admixed with a suitable diluent, carrier or excipient.

In one preferred embodiment the medicament comprises an antibody or antigen obtained from an undifferentiated cell according to the present invention admixed with a suitable diluent, carrier or excipient.

Preferably the medicament is for the treatment of any one of: cancer, autoimmune diseases, blood disorders, cellular or tissue regeneration, organ regeneration, the treatment of organ or tissue transplants, or congenital metabolic disorders.

In a preferred embodiment the present invention relates to a process of introducing a gene into the genome of an undifferentiated cell, wherein the process comprises introducing the gene into a more committed cell, and then preparing an undifferentiated cell by the method according to the present invention, whereby the gene is present in the undifferentiated cell.

In a more preferred embodiment the present invention relates to a process of introducing a gene into the genome of an undifferentiated cell, wherein the process comprises inserting the gene into the genome of a more committed cell, and then preparing an undifferentiated cell by the method according to the present invention, whereby the gene is present in the undifferentiated cell.

In an even more preferred embodiment the present invention relates to a process of introducing the genome of a gene into an undifferentiated cell, wherein the process comprises inserting the gene into the genome of a more committed cell, and then preparing an undifferentiated cell by the method according to the present invention, whereby the gene is present in the genome of the undifferentiated cell.

The present invention encompasses an undifferentiated cell prepared by any one of these processes of the present invention.

As already mentioned, the present invention also encompasses a medicament comprising an undifferentiated cell prepared by any one of these processes admixed with a suitable diluent, carrier or excipient. With such a medicament the undifferentiated cell could be used to produce a beneficial more committed cell, such as one having a correct genomic structure, in order to alleviate any symptoms or conditions brought on by or associated with a more committed cell having an incorrect genomic structure.

Thus, the present invention also provides a process of removing an acquired mutation from a more committed cell wherein the method comprises forming an undifferentiated cell by the method according to the present invention, committing the undifferentiated cell into a recommitted cell, whereby arrangement or rearrangement of the genome and/or nucleus of the cell causes the mutation to be removed.

Preferably the gene is inserted into the immunoglobulin region or TCR region of the genome.

Alternatively, the undifferentiated cell could be used to produce a more committed cell that produces an entity that cures any symptoms or conditions brought on by or associated with a more committed cell having an incorrect genomic structure.

For example, the present invention may be used to prepare antibodies or T cell receptors to an antigen that is expressed by the more committed cell which has retrodifferentiated into the undifferentiated cell. In this regard, the antigen may be a fetospecific antigen or a cross-reactive fetospecific antigen.

The present invention also includes a process of controlling the levels of undifferentiated cells and more committed cells. For example, the present invention includes a method comprising forming an undifferentiated cell by the method according to the present invention and then activating an apoptosis gene to affect the undifferentiated cell, such as bring about the death thereof.

In one preferred embodiment of the present invention, the more committed cell is not a cancer cell. In another preferred embodiment of the present invention, the agent is neither carcinogenic nor capable of promoting cancer growth.

The present invention also covers a method of treating a patient suffering from a disease or a disorder resulting from a defective cell or an unwanted cell, the method comprising preparing an undifferentiated cell by contacting a more committed cell with an agent that causes the more committed cell to retrodifferentiate into the undifferentiated cell, and then optionally committing the undifferentiated cell into a recommitted cell; wherein the undifferentiated cell, or the recommitted cell, affects the defective cell or the unwanted cell to alleviate the symptoms of the disease or disorder or to cure the patient of the disease or condition.

In summation, the present invention relates to the preparation of an undifferentiated cell from a more committed cell.

The present invention will now be described by way of example, in which reference shall be made to the following Figures:

A. Materials and Methods

Patients

Figure 1:
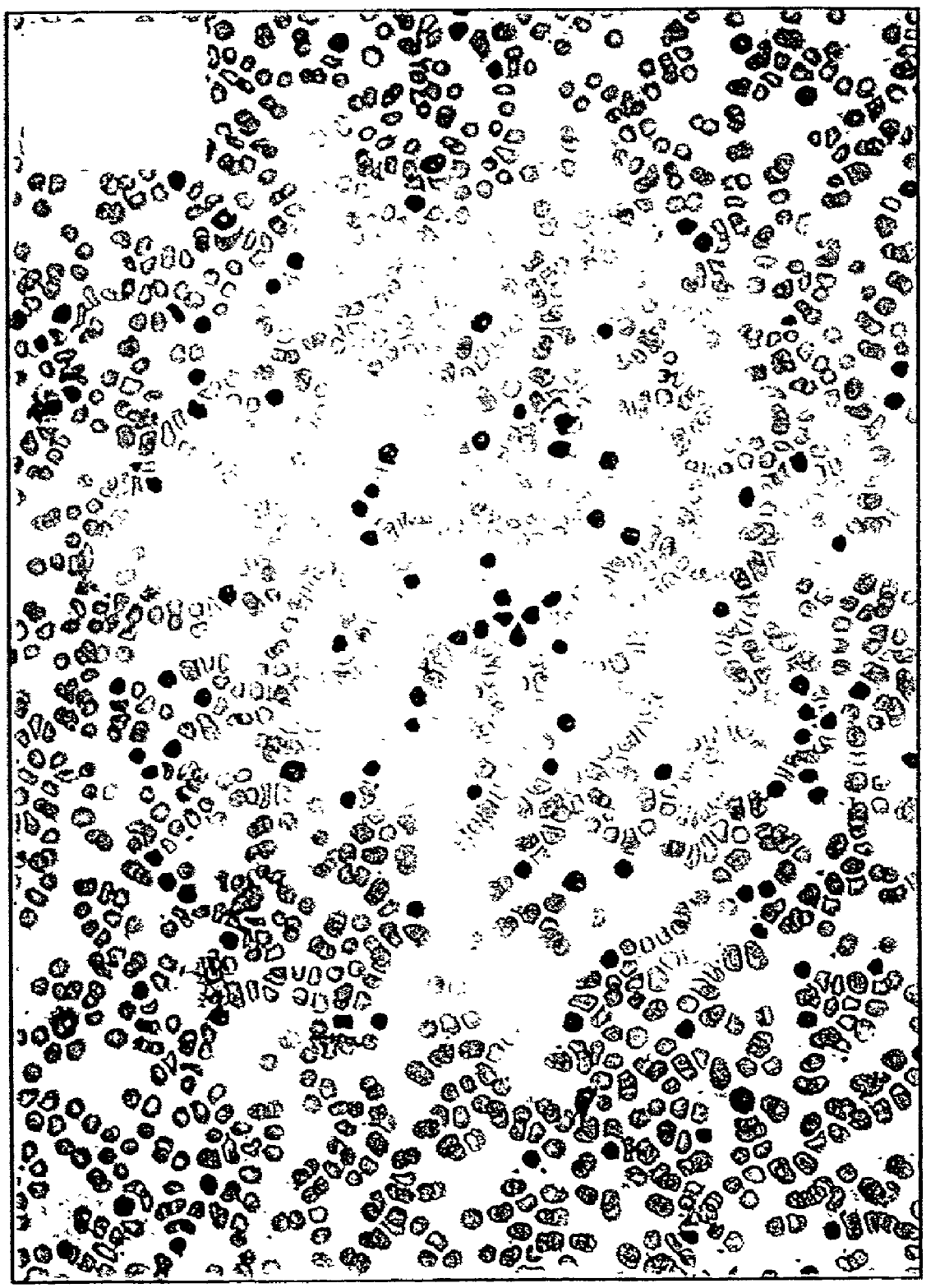
FIG. 1 which is a microscope picture of cells before the method of the present invention.

Blood samples were obtained in lavender top tubes containing EDTA from patients with B-cell chronic lymphocytic leukaemia's, patients with antibody deficiency (including IgA deficiency and X-linked infantile hypogammaglobulinaemias), patients with HIV infections and AIDS syndrome, a patient with CMV infection, a patient with Hodgkin's lymphomas, a patient with acute T-cell leukaemia, a 6-days old baby with Hodgkin's lymphomas, a patient with acute T-cell leukaemia, a 6-days old baby with blastcytosis, various patients with various infections and clinical conditions, cord blood, bone marrow's, and enriched B-lymphocyte preparations of healthy blood donors.

Clinical and Experimental Conditions

The clinical and experimental treatment conditions of patients, including various types of treatment applied to their blood samples, are described in Table 1. Differential white blood cell (WBC) counts were obtained using a Coulter Counter and these are included in the same Table.

Treatment of Blood

Blood samples, once obtained, were treated with pure monoclonal antibody to the homologous region of the β-chain of the HLA-DR antigen (DAKO) and left to mix on a head to head roller at room temperature for a maximum of 24 hours. Some samples were mixed first on a head to head roller for 15 minutes after which they were left to incubate in an incubator at 22° C. The concentration of monoclonal antibody added to blood samples varied from 10–50 µl/ml of blood.

In addition, other treatments treatments were applied at the same concentrations and these included addition of a monoclonal antibody to the homologous of the α-chain of the HLA-DR antigen, a monoclonal antibody to the homologous region of class I antigens, a monoclonal antibody to CD4, a monoclonal antibody to CD8, and a PE conjugated monoclonal antibody to the homologous region of the β-chain of the HLA-DR antigen.

Other treatments included the simultaneous addition of monoclonal antibodies to the homologous regions of the α and β-chains of the HLA-DR antigen to blood samples.

Furthermore, alkylating agents such as cyclophosphoamide were added to blood samples in combination with pure monoclonal antibody to the homologous region of the β-chain of the HLA-DR antigen.

Following these treatments blood samples were stained with panels of labelled monoclonal antibodies as instructed by the manufacturer's instructions and then analyzed using flow cytometry.

Incubation periods with monoclonal antibodies ranged from 2 hour, 4 hour, 6 hour, 12 hour to 24 hour intervals.

Labelled Antibodies

The following monoclonal antibodies were used to detect the following markers on cells by flow cytometry: CD19 and CD3, CD4 and CD8, DR and CD3, CD56 & 16 and CD3, CD45 and CD14, CD8 and CD3, CD8 and CD28, simultest control (IgG1 FITC+IgG2a PE), CD34 and CD2, CD7 and CD13 & 33, CD10 and CD25, CD5 and CD10, CD5 and CD21, CD7 and CD5, CD13 and CD20, CD23 and CD57 and CD25 and CD45 RA (Becton & dickenson and DAKO).

Each patient's blood sample, both treated and untreated, was analyzed using the majority of the above panel in order to account for the immunophenotypic changes that accompanied different types of treatments and these were carried out separately on different aliquots of the same blood sample. Untreated samples and other control treatments were stained and analyzed simultaneously.

Flow Cytometry

Whole blood sample was stained and lysed according to the manufacturer instructions. Flow cytomery analysis was performed on a FACScan@ with either simultest or PAINT A GATE software (BDIS) which included negative controls back tracking. 10,000 to 20,000 events were acquired and stored in list mode files.

Morphology

Morphology was analyzed using microscopy and Wright's stain.

B. Results

CD19 and CD3 Panel

Treatment of blood samples with monoclonal antibody to the homologous region of the β-chain of the HLA-DR antigen always decreased the relative number of $CD19^+$ cells. This marker is a pan B-cell antigen (see Table). This antigen is present on all human B lymphocytes at all stages of maturation but is lost on terminally differentiated plasma cells. Hence, this is an indication that B cells were retrodifferentiating into undifferentiated cells.

The same treatment caused the relative number of $CD3^+$ cells to increase dramatically especially in blood of patients with B-CLL, which was always accompanied by an increase in the relative number in $CD3^-CD19^-$ cells. CD3 is present on all mature T-lymphocytes and on 65%–85% of thymocytes. This marker is always found in association with α-/β- or gamma/delta T-cell receptors (TCR) and together these complexes are important in transducing signals to the cell interior. Hence, this is an indication that B cells were retrodifferentiating into undifferentiated cells and then being committed to new differentiated cells, namely T cells.

A novel clone of cells appeared in treated blood of B-CLL patients co-expressing the CD19 and CD3 markers—i.e. $CD19^+$ and $CD3^+$ cells (see Charts 1, patient 2, 3 & 4 at 2 hr, 6 hr & 24 hr of starting treatment). Other patients with different conditions showed an increase in the relative number of these clones of cells. These cells were exceptionally large and heavily granulated and extremely high levels of CD19 were expressed on their cell membrane. The CD3 marker seems to be expressed on these cells at similar levels to those expressed on normal mature lymphocytes.

In Table 2, patient numbers 2, 3 and 4 are actually numbers representing the same patient and their delineation was merely to show the effect of treatment on blood with time (See Table 1 for experimental and clinical condition of this patient).

The $CD19^+CD3^+$ clones in treated samples seem to decrease with time, reaching original levels to those determined in untreated sample at 2 hrs, 6 hrs and 24 hrs time.

Another type of cell of the same size and granularity was detected in treated samples and these cells had high levels of CD19 expressed on their surface but were negative for the CD3 marker and rich in FC receptors. However, the relative number of these cells appeared to decrease in time. Of interest, at 24 hours treatment of blood sample (2, 3 and 4) there was a decrease in the relative number of $CD19^-CD3^-$ cells in a group of cells that were initially observed to increase after 2 and 6 hr's treatment of blood samples. However, Coulter counts of WBC populations were reduced on treatment of blood with monoclonal antibody to the homologous region of the β-chain of the HLA-DR antigen. This finding suggests that this type of treatment gives rise to atypical cells that cannot be detected by Coulter (Table 1) but can be accounted for when measured by flow cytometry which counts cells on the basis of surface markers, size and granularity. Furthermore, these atypical cells were accounted for by analysing morphology using Wright's stain under a microscope. Flow cytometric charts of these phenomena are represented in Charts (1, 2, 3 & 4) and the immunophenotypic changes obtained on treatment of blood samples seems to suggest that $CD19^+$ and $CD3^+$ lymphocytes are an interconnected group of cells but remain distinct on the basis of CD19 and CD3 relative expression compared to stem cells.

In Table 2, patient numbers 5 and 6 represent the same patient but analysis of treated and untreated blood samples were monitored with time and at the same time (see Table 1).

Patients blood with no B-cell malignancy showed similar trends of immunophenotypic changes when compared to blood of B-CLL patients but the changes were not to the same extent. However, the relative and absolute number of B-lymphocytes and MHC class II positive cells in the blood of these patients are extremely low compared to those found in the blood of B-CLL patients.

Two brothers both with X-linked infantile hypogammaglobulinemia who were B cell deficient showed different immunophenotypic changes in the relative number of $CD3^+$ cells on treatment of their blood. The younger brother who was 2 months old and not ill, on treatment of his blood, showed a slight increase in the relative number of $CD3^+$ cells which was accompanied by a decrease in the relative number of $CD3^-$ $CD19^-$ cells. On the other hand, the other brother who was 2 years old and was extremely sick and with a relatively high number of activated T cells expressing the DR antigens showed a decrease in the number of $CD3^-$ cells on treatment of his blood. No other markers were used to measure other immunophentypic changes that might have occurred because the blood samples obtained from these two patients were extremely small (Table 2, ID 43/BD and 04/BD).

Patient 91 in Table 2 shows a decrease in the relative number of $CD3^+$ cells following treatment of blood which was accompanied by an increase in the relative number of $CD3^-CD19^-$ cells. However, on analysis of other surface markers such as CD4 and CD8 (see Table 3) the patient was observed to have a high relative number of $CD4^+CD8^-$ cells in his blood and this was noted prior to treatment of blood samples with monoclonal antibody to the β-chain of the DR antigen and these double positive cells decreased appreciably following treatment of blood. Furthermore, when further markers were analyzed the relative number of $CD3^+$ cells were seen to have elevated (See Table 4).

An enriched preparation of B-lymphocytes obtained from healthy blood donors when treated with monoclonal antibody to the β-chain of DR antigens showed a dramatic increase in the relative number of $CD3^+$ cells which were always accompanied by a decrease in the relative number of $CD19^+$ cells and by an increase in the relative number of $CD19^+CD3^-$ cells. Further analysis using markers such as CD4 and CD8 show a concomitant increase in the relative number of these markers. However, an enriched preparation of T lymphocytes of the same blood donors when treated with the same monoclonal antibody did not show the same changes.

CD4 and CD8 Panel

The CD4 antigen is the receptor for the human immunodificiency virus. The CD4 molecule binds MHC class II antigen in the B2 domain, a region which is similar to the CD8 binding sites on class I antigens. Binding of CD4 to class II antigen enhances T cell responsiveness to antigens and so does the binding of CD8 to class I antigens. The CD8 antigens are present on the human supressor/cytotoxic T-lymphocytes subset as well as on a subset of natural killer (NK) lymphocytes and a majority of normal thymocytes. The CD4 and CD8 antigens are coexpressed on thymocytes and these cells lose either markers as they mature into T-lymphocytes.

On analysis of the CD4 and CD8 markers—see below—and from a majority of blood samples presented in Table 2, a pattern of staining emerges which supports the presence of a retrodifferentiation process of B-lymphocytes into undifferentiated cells and the subsequent differentiation into T-lymphocytes.

$CD4^+CD8^+$ cells, which are double positive cells, always appeared following treatment of blood samples with monoclonal antibody to the homologous region of the β-chain and these types of cells were markedly increased in the blood of treated samples of patients with B-CLL and which were absent altogether in untreated samples (See Table 3 and Charts 1, 2 3 & 4). In the same specimens the relative number of single positive cells such as $CD8^+$ and $CD4^+$ cells was also noted to increase simultaneously. Furthermore, a decrease in the relative number of $CD4^- CD8^-$ cells which, at least in the case of B-CLL correspond to B cells was noted to fall dramatically in treated samples when compared to untreated specimens which remained at the same level when measured with time. However, measurement of the relative number of $CD4^+CD8^+$ cells with time in treated samples showed that there was a concomitant increase in the number of single positive cells with a decrease in the relative number of double positive cells. This type of immunophenotypic change is characteristic of thymic development of progenitor cells of the T-lymphocyte lineage in the thymus (Patient number 2, 3 and 4). The CD4 antigen is present on the helper/inducer T-lymphocyte subsets ($CD4^+CD3^+$) and a majority of normal thymocytes. However, this antigen is present in low density on the cell surface of monocytes and in the cytoplasm of monocytes and macrophages ($CD3^- CD4^+$).

The relative number of $CD4^+$ low cells was affected differently in different blood samples following treatment. The relative number of this type of cells seems unaffected in blood samples of patients with B-CLL following treatment when compared to untreated samples. Such low levels of CD4 expression is found on monocytes and very early thymocytes.

Patient $HIV^+25$ on treatment showed a substantial increase in the number of double positive cells expressing CD4 and CD8 simultaneously. On the other hand, patient 91 on treatment showed a decrease in this subtype of cells and the observation of such phenomenon is time dependent. The relative number of $CD8^+$ cells was observed to increase in untreated blood samples of patients with B-CLL when measured with time whereas the relative number of $CD4^+$ and $CD4^-$ low cells was observed to decrease at the same times (Table 3 patient 2, 3 and 4).

DR and CD3 Panel

The DR markers are present on monocytes, dendritic cells, B-cells and activated T-lymphocytes.

Treated and untreated samples analysed with this panel showed similar immunophenotypic changes to those obtained when blood samples were analysed with the CD19 and CD3 markers (see Table 2) and these antigens as mentioned earlier are pan B and T-cell markers respectively.

Treatment of blood with monoclonal antibodies seems to affect the relative number of $DR^+$ B-lymphocytes so that the level of DR+ cells decrease. In contrast, the relative number of $CD3^+$ (T-cells) cells increase significantly (see Table 4 and Chart).

Furthermore, the relative number of activated T cells increased in the majority of treated blood samples of patients with B-CLL and these types of cells were affected variably in treated samples of patients with other conditions. Furthermore, the relative number of DR high positive cells appeared in significant numbers in treated samples of patients with B-CLL and a 6 day old baby with increased $DR^+ CD34^+$ blasts in his blood. However, it should be noted that the blasts which were present in this patient's blood were negative for T and B-cell markers before and after treatment but became more positive for myeloid lineage antigens following treatment. The relative number of $CD3^-$ $DR^-$ cells increased in the majority of treated blood samples and was proportional to increases in the relative number of $CD3^+$ cells (T-cells) and was inversely proportional to decreases in the relative number of DR+ cells (B-cells).

CD56&16 and CD3 Panel

The CD56&CD16 markers are found on a heterogeneous group of cells, a subset of lymphocytes known generally as large granular lymphocytes and natural killer (NK) lymphocytes. The CD16 antigen is expressed on virtually all resting NK lymphocytes and is weakly expressed on some $CD3^+$ T lymphocytes from certain individuals. This antigen is found on granulocytes in lower amount and is associated with lymphocytes containing large azurophilic granules. The CD16 antigen is the IgG FC receptor III.

A variable number of $CD16^+$ lymphocytes coexpress either the CD57 antigen or low-density CD8 antigen or both. In most individuals, there is virtually no overlap with other T-lymphocyte antigens such as the CD5, CD4, or CD3 antigens. The CD56 antigen is present on essentially all resting and activated $CD16^+$ NK lymphocytes and these subsets of cells carry out non-major histocompatibility complex restricted cytotoxicity.

Immunophenotyping of treated and untreated blood samples of B-CLL and some other patients with other conditions showed an increase in the relative number of cells coexpressing the CD56&CD16 antigens which were heavily granulated and of medium size (see Table 5 and Charts 1, 2, 3 & 4). These observations were also accompanied by a marked increase in the relative number of cells expressing the CD3 antigen only (without the expression of CD56 and CD16 markers) and cells coexpressing the CD56&CD16 and CD3 markers together.

In Table 5, patient numbers 2, 3, and 4 represent the same blood sample but being analysed at 2 hours, 6 hours and 24 hours respectively (before and after treatment). This sample shows that treatment of blood with monoclonal antibody to the homologous region of the β-chain of DR antigen seems to cause spontaneous production of $CD56^+$ and $CD16^+$ cells, $CD3^+$ cells and $CD56^+$ and $CD16^+$ $CD3^+$ cells and these observations were always accompanied by the disappearance of B-cell markers (CD19, DR, CD56, $CD16^- CD3^-$).

Onward analysis of this blood sample before and after treatment showed the levels of CD56+ and CD16+ cells to decrease with time and the level of CD3+ cells to increase with time.

Blood samples of patient 7 with B-CLL, did not show any changes in the number of cells expressing the CD56, CD16 and CD3 antigens when compared to inmmunophenotypic changes observed in treated and untreated samples and this is because the amount of monoclonal antibody added was extremely low relative to the number of B lymphocytes. However, treatment of this patient's blood sample on a separate occasion with an appropriate amount of monoclonal antibody showed significant increases in the relative number of CD3+, CD56+ & CD16+ and CD56+ and CD16+ CD3+ cells.

Blood samples of other patients with other conditions showed variable changes in the level of these cells and this seems to be dependent on the number of B-lymphocytes present in blood before treatment, duration of treatment and probably the clinical condition of patients.

CD45 and CD14 Panel

The CD45 antigen is present on all human leukocytes, including lymphocytes, monocytes, polymorphonuclear cells, eosinophils, and basophils in peripheral blood, thymus, spleen, and tonsil, and leukocyte progenitors in bone marrow.

The CD14 is present on 70% to 93% of normal peripheral blood monocytes, 77% to 90% of pleural or peritoneal fluid phagocytes. This antigen is weakly expressed on granulocytes and does not exist on unstimulated lymphocytes, mitogen-activated T lymphocytes, erythrocytes, or platelets.

The CD45 antigen represents a family of protein tyrosine phosphatases and this molecule interacts with external stimuli (antigens) and effects signal transduction via the Scr-family members leading to the regulation of cell growth and differentiation.

Engagement of the β-chain of the DR antigens in treated blood samples especially those obtained from patients with B-CLL suggests that such a treatment affects the level of CD45 antigens on B-lymphocytes. The overall immunophenotypic changes that took place on stimulation of the β-chain of the DR antigen seem to give rise to different types of cells that can be segregated on the basis of the level of CD45 and CD14 expression as well as morphology as determined by forward scatter and side scatter (size and granularity respectively) and these results are presented in Table 6 and Charts (1, 2, 3, 4 & 5).

On treatment the relative number of CD45 low cells (when compared to untreated samples) increased significantly and so did the relative number of cells co-expressing the CD45 and CD14 antigens. This type of immunophenotypic changes coincided with a decrease in the relative number of CD45 high cells (compared to untreated samples). However, this latter population of cells can be further divided on the basis of morphology and the degree of CD45 expression. One type was extremely large and had extremely high levels of CD45 antigen when compared to the rest of cells present in the charts (see charts 1, 2, 3 and 4). On analysis of this panel following treatment with time (see Table patient 2, 3 and 4 and charts) the relative number of CD45+ cells initially fell drastically with time to give rise to CD45 low cells. However, analysis of blood 24 hours later showed the opposite situation.

Samples 5 and 7 reveal opposite immunophenotypic changes to those obtained with other samples obtained from other B-CLL patients and this is because the samples were analysed at a much earlier incubation time with the monoclonal antibody. In fact the sequential analysis of blood samples after treatment seems to suggest that the immunophenotypic changes undertaken by B lymphocytes is time dependent because it represents a stage of development and the immunophenotypic changes measured at time X is not going to be the same at time X plus (its not fixed once induced). However, these types of changes must be occurring in a more stringent manner in the body otherwise immunopathology would ensue. The effect of treatment of blood samples from other patients with no B-cell malignancy show variable changes in immunophenotypes of cells and this because B-lymphocytes are present in lower amount. However, treatment of enriched fractions of B-lymphocytes obtained from healthy blood donors show similar immunophenotypic changes to those obtained with B-CLL with high B lymphocyte counts.

CD8 and CD3 Panel

The CD8 antigenic determinant interacts with class I MHC molecules, resulting in increased adhesion between the CD8+ T lymphocytes and the target cells. This type of interaction enhances the activation of resting lymphocytes. The CD8 antigen is coupled to a protein tyrosine kinase (p56ick) and in turn the CD8/p56ick complex may play a role in T-lymphocyte activation.

Treatment of blood samples obtained from patients with B-CLL with monoclonal antibody to the B chain causes a significant increase in the relative number of CD3CD8 and CD3 (highly likely to be CD4CD3) positive cells thus indicating more clearly that double positive cells generated initially are undergoing development into mature T-lymphocytes. This is a process that can be measured directly by CD19 and by DR and indirectly by CD8−CD3− antigens. Serial assessment of treated blood samples of the same patient with time seems to agree with a process which is identical to thymocyte development (Table 7, patient 2, 3 and 4 and Chart 1).

The relative number of CD8+ cells increased with time in treated and untreated samples but to a higher extent in untreated samples. On the other hand, the relative number of CD8+CD3+ cells decreased with time in untreated samples. However, the relative number of CD3+ cells increased in treated blood samples when measured with time and these types of cells highly correspond to CD4+CD3+ single positive cells; a maturer form of thymocytes. In addition, since these samples were also immunophenotyped with other panels (mentioned above in Tables 3, 4, 5 and 6) the overall changes extremely incriminate B cells in the generation of T lymphocyte progenitors and progenies.

Blood samples from a patient with B-CLL (number 2, 3 and 4 Tables 1, 2, 3, 4, 5, 6, 7) in separate aliquots were treated with nothing, PE conjugated monoclonal antibody to the homologous region of the β-chain of DR antigen and unconjugated form of the same monoclonal antibody. On comparison of PE conjugated treatment clearly indicates no change in the relative number of CD3 positive cells and associated markers such as CD4 which have been observed in significant levels when the same blood sample was treated with unconjugated form of the antibody. However, an increase in the number of CD45 positive cells with no DR antigen being expressed on their surface was noted when measured with time (see Table 8). A finding that was similar to that noted in untreated samples when immunophenotyped with time (Table 6). Furthermore, the relative number of cells expressing CD45 low decreased in time, a phenomenon which was also noted in the untreated samples (when measured with time) of the same patient (see chart 1A).

C. Comparison of the Effect of other Monoclonal Antibodies with Different Specificity on T-Lymphophoiesis CD19 and CD3 Panel Treatment of blood samples with monoclonal antibody to the homologous region of the α-chain of the DR antigen and the homologous region of MHC Class I antigens decreased the number of CD3$^+$ cells and increased the number of CD19$^+$ cells. Treatment of the same blood with monoclonal antibody to the homologous region of the β-chain of the DR antigen decreased the number of CD19$^+$ cells and increased the number of CD3$^+$ cells. Treatment with the latter monoclonal antibody with cyclophosphoamide revealed the same effect (Table 14 patient 5/6 with B-CLL at 2 hr treatment).

Onward analysis of CD19$^+$ and CD3$^+$ cells in the same samples revealed further increases in the relative number of CD3$^+$ cells only in blood treated with monoclonal antibody to the homologous region of the β-chain of DR antigen (Table 14 patient 5/6 at 24 hours following treatment). However, onward analysis (24 hours later patient 5/6 Table 14) of blood samples treated with cyclophosphamide plus monoclonal antibody to the β-chain of DR antigen show reversal in the relative number of CD19$^+$ and CD3$^+$ cells when compared to that observed at 2 hour incubation time under exactly the same condition.

In general, treatment of blood samples of the same patient with monoclonal antibody to the homologous region of the α chain of the DR antigen or monoclonal antibody to the homologous of the α-chain of the class I antigen shows an increase in the relative number of CD19$^+$ cells (pan B marker) when compared to untreated sample. The relative number of CD19$^-$CD3$^-$ cells decreased slightly in blood samples treated with monoclonal antibody to the α-chain of DR antigen or treated with monoclonal antibody to class I antigens (see Table 14 & Charts 2, 3 & 4). Treatment of blood samples of patient 09 with monoclonal antibody to class I antigens increased the relative number of CD3$^+$ cells and decreased slightly the relative number of CD19$^+$ and CD19$^-$CD3$^-$ cells. However, treatment of an enriched preparation of B-lymphocytes obtained from healthy blood donors with monoclonal antibody to the β-chain or α-chain of DR antigen showed similar immunophenotypic changes to those obtained with patient with B-CLL.

Treatment of HIV$^+$ and IgA deficient patients with monoclonal antibody to the β-chain of the DR antigen increased the relative number of CD3$^+$ cells and decreased the relative number of CD19$^+$ cells. However, treatment of the same blood sample with monoclonal antibody to the homologous region of class I antigen did not produce the same effect. Treatment of blood samples obtained from patients (34/BD and 04/BD) with B-cell deficiency showed variable immunophenotypic changes when treated with monoclonal antibodies to the β-chain of the DR antigen, class I antigens and CD4 antigen.

CD4 and CD8 Panel

Blood samples analysed using the CD19 and CD3 panel (Table 14) were also immunophenotyped with the CD4 and CD8 panel (Table 15). Both panels seem to agree and confirm each other. Incubation for 2 hours of blood samples of patients with B-CLL (Table 15, patients 5/6 and 10, Charts 2, 3 & 4) with monoclonal antibody to the homologous region of the β-chain of the DR antigen or with this monoclonal antibody plus cyclophosphoamide increased the relative number of CD8$^+$ and CD4$^+$ cells and cells coexpressing both markers. On the other hand, treatment of the same samples with monoclonal antibodies to the homologous region of the α-chain of the DR antigen or the homologous region of the α-chain of class I antigen did not produce the same effects.

Comparison of immunophenotypic trends obtained at 2 hours and 24 hours incubation periods with monoclonal antibody to the β-chain of the DR antigen plus cyclophosphoamide revealed reverse changes in the relative number of CD4 and CD8 positive cells (Table 15, patient 5/6 with B-CLL at 2 hours and 24 hours) and such changes were in accordance with those obtained when the same blood sample was analysed with the CD19 and CD3 panel (Table 14 the same patient). The later findings indicate that the subsequent differentiation is reversible as the undifferentiated cells can differentiate into T-lymphocytes or B-lymphocytes.

DR and CD3 Panel

The immunophenotypic changes obtained with DR and CD3 (Table 16) panel confirm he findings obtained with CD19 and CD3 panel and CD4 and CD8 panel (Tables 14 & 15 & Charts 2, 3 & 4) which followed treatment of the same blood samples with monoclonal antibodies to the homologous region of the beta- or alpha- side of the DR antigen or monoclonal antibody to class I antigens or monoclonal antibody to the β-chain of the DR antigen plus cyclophosphoamide at 2 hour analysis.

From the results, it would appear that the monoclonal antibody to the homologous region of the β-chain of the DR antigen is extremely capable of driving the production of CD3 positive cells from DR$^+$ cells.

Furthermore, treatments such as those involving engagement of the α-chain of DR antigens or engagement of the β-side of the molecule in conjunction with cyclophosphoamide (prolonged incubation time) promoted increases in the relative number of CD19$^+$ cells or DR$^+$ cells.

CD56&16 and CD3 Panel

Treatment of blood samples, especially of those of patients with B-CLL with high B-lymphocyte counts with monoclonal antibody to the homologous region of the β-chain of the DR antigen increased the relative number of CD56&16 positive cells.

In these patients the relative number of CD3$^+$ and CD56$^+$ and CD16$^+$CD3$^+$ cells also increased following treatment of blood samples with monoclonal antibody to the β-chain, confirming earlier observations noted with the same treatment when the same blood samples were analysed with CD3 and CD19 and DR and CD3 panels.

CD45 and CD14 Panel

Blood samples treated with monoclonal antibodies to the β- or alpha- chains of the DR antigen or to the β-chain plus cyclophosphoamide or class I antigens were also analysed with the CD45 and CD14 panel (Table 18). The delineation of CD45 low, CD45 high and CD45 medium is arbitrary. Treatment of blood sample 5/6 (at 2 hours) with monoclonal antibodies to the β-chain of the DR antigen or with this monoclonal antibody plus cyclophosphoamide generated CD45$^+$ low cells and increased the relative number of CD45$^+$ medium cells. However, the former treatment increased the relative number of CD45$^+$ high cells and the latter treatment decreased the relative number of CD45$^+$ medium cells and these changes appeared to be time dependent.

Blood samples of patient 5/6 and 10 (B-CLL) on treatment with monoclonal antibody to class I antigens showed a decrease in the relative number of CD45$^+$ medium cells and similar observations were noted in blood samples 09 and HIV+ following the same treatment when compared to untreated samples. Treatment of blood samples of HIV+ and IgA/D patients with monoclonal antibody to class I antigen increased the relative number of CD45+ low cells when compared to untreated samples or samples treated with monoclonal antibody to the β-chain of the DR antigen. However, blood samples of these patients showed a decrease in the relative number of CD45+ medium cells on treatment with monoclonal antibody to the homologous regions of the β-chain of the DR antigen. Medium CD45+ cells increased in blood samples of IgA/D patient following monoclonal antibody to class I antigen treatment. Cells that were extremely large, heavily granular and expressing intense levels of CD45 antigen were noted in treated blood samples with monoclonal antibody to the homologous region of the β-chain of DR antigen of MHC class II antigens (see Charts 1, 2, 3, 4 & 5).

CD8 and CD28 Panel

The CD28 antigen is present on approximately 60% to 80% of peripheral blood T (CD3+) lymphocytes, 50% of CD8+ T lymphocytes and 5% of immature CD3-thymocytes. During thymocyte maturation, CD28 antigen expression increases from low density on most CD4+CD8+ immature thymocytes to a higher density on virtually all mature CD3+, CD4+ or CD8+ thymocytes. Cell activation further augments CD28 antigen density. Expression of the CD28 also divides the CD8+ lymphocytes into two functional groups. CD8+CD28+ lymphocytes mediate alloantigen-specific cytotoxicity, that is major histocompatibility complex (MHC) class I-restricted. Suppression of cell proliferation is mediated by the CD8+CD28− subset. The CD28 antigen is a cell adhesion molecule and functions as a ligand for the B7/BB-1 antigen which is present on activated B lymphocytes.

Treatment of blood samples of patients (Table 19, patients 5/6 and 8) with B-CLL with monoclonal antibody to the homologous region of β-chain of the DR antigen increased the relative number of CD8+, CD28+ and CD8+CD28+ cells and all other types of treatments did not.

CD34 and CD2 Panel

The CD34 antigen is present on immature haematopoietic precursor cells and all haematopoietic colony-forming cells in bone marrow, including unipotent (CFU-GM, BFU-E) and pluripotent progenitors (CFU-GEMM, CFU-Mix and CFU-blast). The CD34 is also expressed on stromal cell precursors. Terminal deoxynucleotidyl transferase (TdT)+ B- and T-lymphoid precursors in normal bone are CD34+. The CD34 antigen is present on early myeloid cells that express the CD33 antigen but lack the CD14 and CD15 antigens and on early erythroid cells that express the CD71 antigen and dimly express the CD45 antigen. The CD34 antigen is also found on capillary endothelial cells and approximately 1% of human thymocytes. Normal peripheral blood lymphocytes, monocytes, granulocytes and platelets do not express the CD34 antigen. CD34 antigen density is highest on early haematopoietic progenitor cells and decreases as the cells mature. The antigen is absent on fully differentiated haematopoietic cells.

Uncommitted CD34+ progenitor cells are CD38−, DR− and lack lineage-specific antigens, such as CD71, CD33, CD10, and CD5, while CD34+ cells that are lineage-committed express the CD38 antigen in high density.

Most CD34+ cells reciprocally express either the CD45RO or CD45RA antigens. Approximately 60% of acute B-lymphoid leukaemia's and acute myeloid leukaemia express the CD34 antigen. The antigen is not expressed on chronic lymphoid leukaemia (B or T lineage) or lymphomas. The CD2 antigen is present on T lymphocytes and a subset of natural killer lymphocytes (NK).

The results are shown in Charts 2, 3 and 5.

Analysis of blood samples of a patient with B-CLL (Table 20, patient 5/6 at 2hours) after treatment with monoclonal antibodies to the β-chain of the DR antigen or the α-chain of the same antigen revealed marked increases in the relative number of CD34+ and CD34+CD2+ cells after treatment with the former antibody. Since the same blood samples were immunophenotyped with the above mentioned panels (see Tables 14 to 19 ) for other markers the increase in the relative number of CD34+ and CD34+CD2+ cells observed here seems to coincide with increases in the relative number of CD4+CD8+, CD8+CD3+ and CD4+CD3+ single positive (SP) cells. Furthermore, these findings which seem exclusive to engagement of the β-chain of the HLA-DR antigen, are in direct support that the process is giving rise to T-lymphopoiesis via B lymphocyte regression.

On analysing the same treatment 24 hours later the CD34+ cells seemed to decrease in levels to give rise to further increase in the relative number of T lymphocytes. The process of retrodifferentiation that initially gave rise to T-lymphopoiesis can be reversed to give rise to B-lymphopoiesis. The former phenomenon was observed at 2 hours incubation time with monoclonal antibody to the β-chain of the HLA-DR antigen plus cylophosphoamide, whereas the latter process was noted at 24 hours incubation time with the same treatment in the same sample (Chart 2).

Treatment of blood samples of HIV+ patient (Table 20 patient HIV+) with monoclonal antibody to the β-chain of the HLA-DR antigen markedly increased the relative number of CD34+ and CD2+CD34+ cells and so did treatment of the same blood sample with monoclonal antibody to the β-chain of the HLA-DR antigen and monoclonal antibody to the α-chain of the same antigen when added together. However, treatment of this blood sample with monoclonal antibody to the α-chain of the HLA-DR antigen did not affect the level of CD34+ cells. Treatment of blood samples obtained from a 6-day old baby (BB/ST Table 20) who was investigated at that time for leukaemia and who had very high number of atypical cells (blasts) in his blood with monoclonal antibody to the β-chain of the HLA-DR antigen, or monoclonal antibody to the α-chain of the same antigen or both monoclonal antibodies added together resulted in the following immunophenotypic changes.

On analysis of untreated blood samples the relative number of CD34+ and DR+ cells were markedly increased and on treatment with monoclonal antibody to the β-chain the relative number of CD34+ cells further increased but were noted to decrease on treatment with monoclonal antibody to the α-chain of the HLA-DR antigen or treatment with monoclonal antibodies to the α and β-chains of the molecule when added together. However, the latter treatment increased the relative number of CD34+CD2+ cells and the opposite occurred when the same blood sample was treated with monoclonal antibody to the β-chain of the HLA-DR antigen alone. On analysis of treated and untreated blood aliquots of the same patient 24 hours later the relative number of CD34+ decreased with all above mentioned treatments except it was maintained at a much higher level with monoclonal antibody to the β-chain of the HLA-DR antigen treatment. The latter treatment continued to decrease the relative number of CD34+CD2+ cells 24 hours later.

These results indicate that engagement of the HLA-DR antigen via the β-chain promotes the production of more CD34+ cells from CD2+CD34+ pool or from more mature types of cells such as B-lymphocytes of patients with B-CLL and these results indicate that this type of treatment promotes retrodifferentiation. However, immunophenotyping of blood samples 24 hours later suggests that these types of cells seem to exist in another lineage altogether and in this case cells seem to exist or rather commit themselves to the myeloid lineage which was observed on analysis of treated blood sample with the CD7 and CD13&33 panel.

Morphology changes immunophenotypic characteristics of B-lymphocytes of B-CLL and enriched fractions of healthy individuals (using CD19 beads) on treatment with monoclonal antibodies to homologous regions of the β-chain of MHC class II antigens. These were accompanied by a change in the morphology of B-lymphocytes. B-lymphocytes were observed colonising glass slides in untreated blood smears were substituted by granulocytes, monocytes, large numbers of primitive looking cells and nucleated red blood cells. No mitotic figures or significant cell death were observed in treated or untreated blood smears.

The results of Table 20 also demonstrate a further important finding in that according to the method of the present invention it is possible to prepare an undifferentiated cell by the retrodifferentiation of a more mature undifferentiated cell.

D. Microscope Pictures

In addition to the antigen testing as mentioned above, the method of the present invention was followed visually using a microscope.

Figure 2:
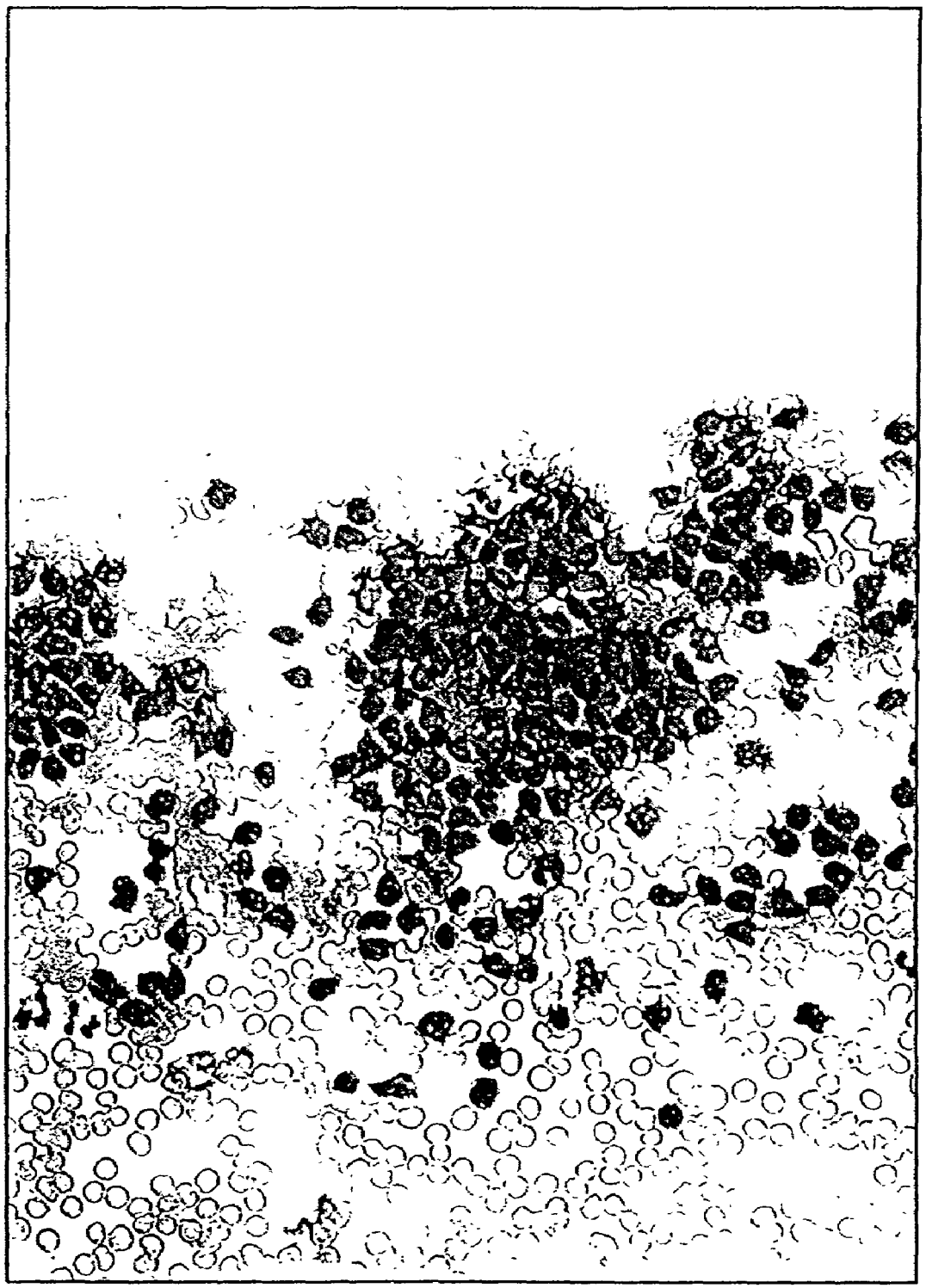
FIG. 2 which is a microscope picture of cells prepared by the method of the present invention.
Figure 3:
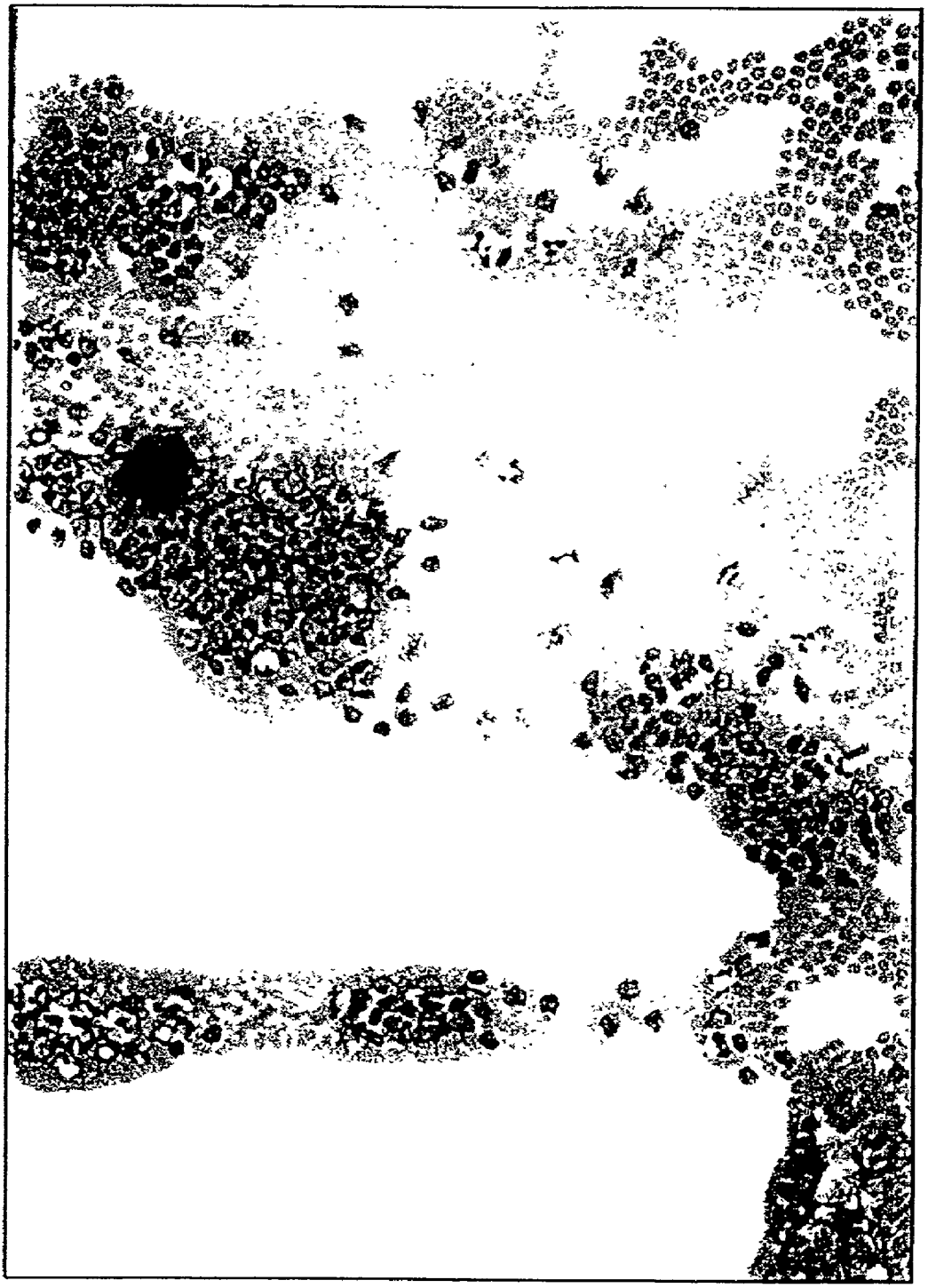
FIG. 3 which is a microscope picture of cells prepared by the method of the present invention but at a lower magnification.

In this regard, FIG. 1 is a microscope picture of differentiated B cells, stained with Wright'S stain before the method of the present invention. FIG. 2 is a microscope picture of undifferentiated cells formed by the retrodifferentiation of the B cells in accordance with the present invention wherein the agent was a monoclonal antibody to the homologous regions of the β-chain of HLA-DR antigen. The undifferentiated cells are the dark stained clumps of cells. FIG. 3 is a microscope picture of the same undifferentiated cells but at a lower magnification.

FIGS. 1 to 3 therefore visually demonstrate the retrodifferentiation of B cells, stained with Wright's Stain to undifferentiated stem cells by the method of the present invention.

Figure 4:
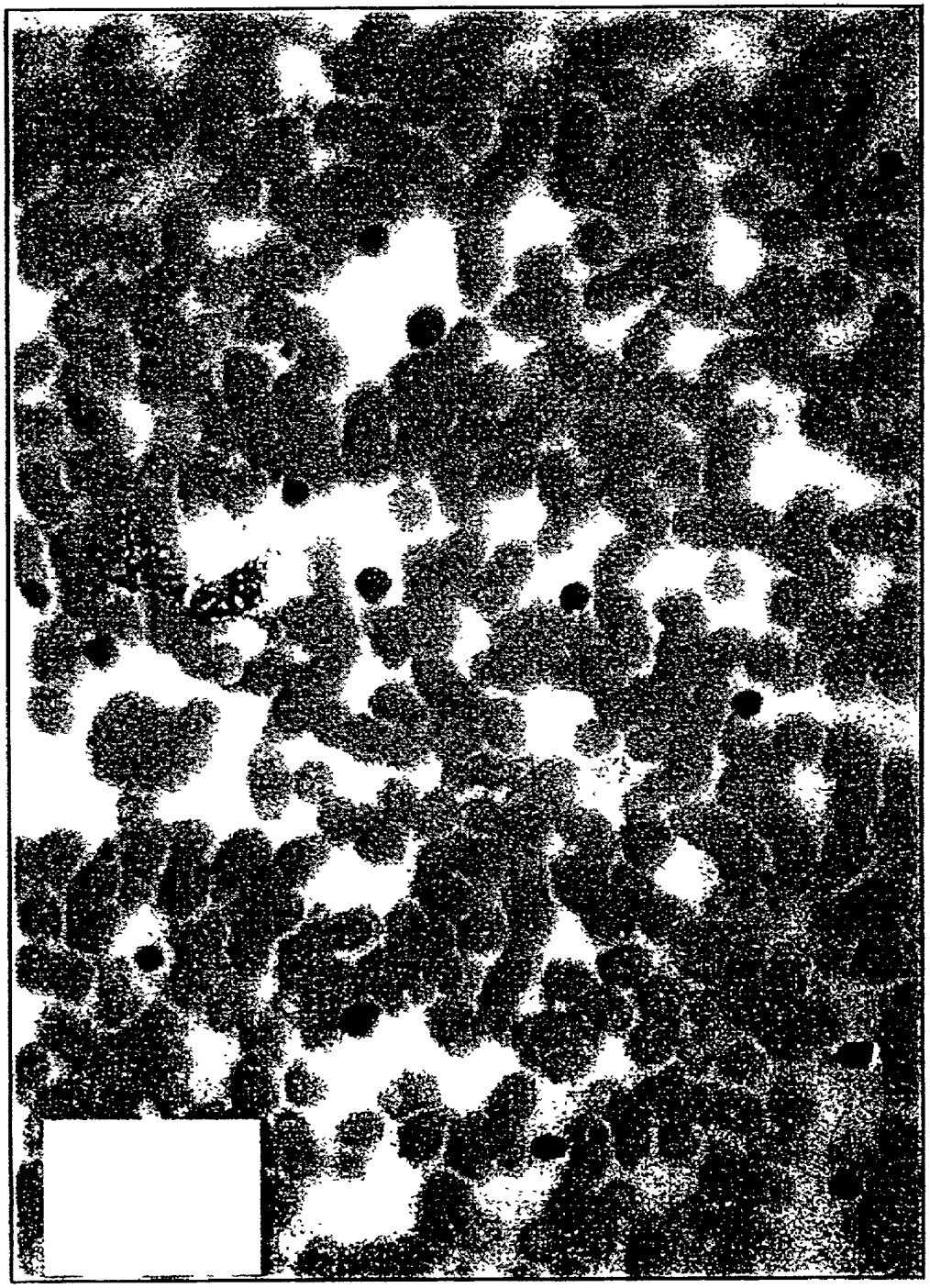
FIG. 4 which is a microscope picture of cells before the method of the present invention.
Figure 5:
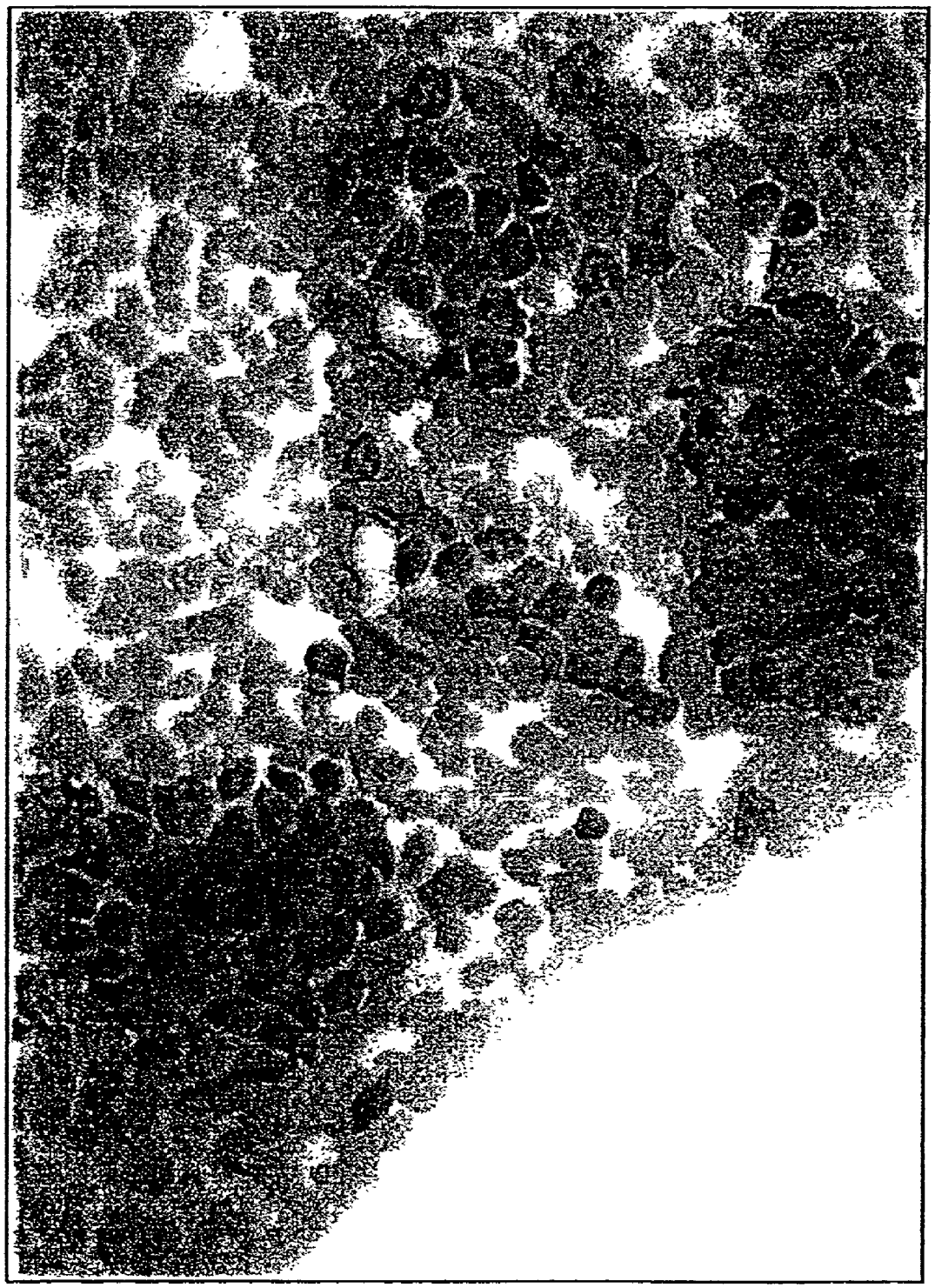
FIG. 5 which is a microscope picture of cells prepared by the method of the present invention.
Figure 6:
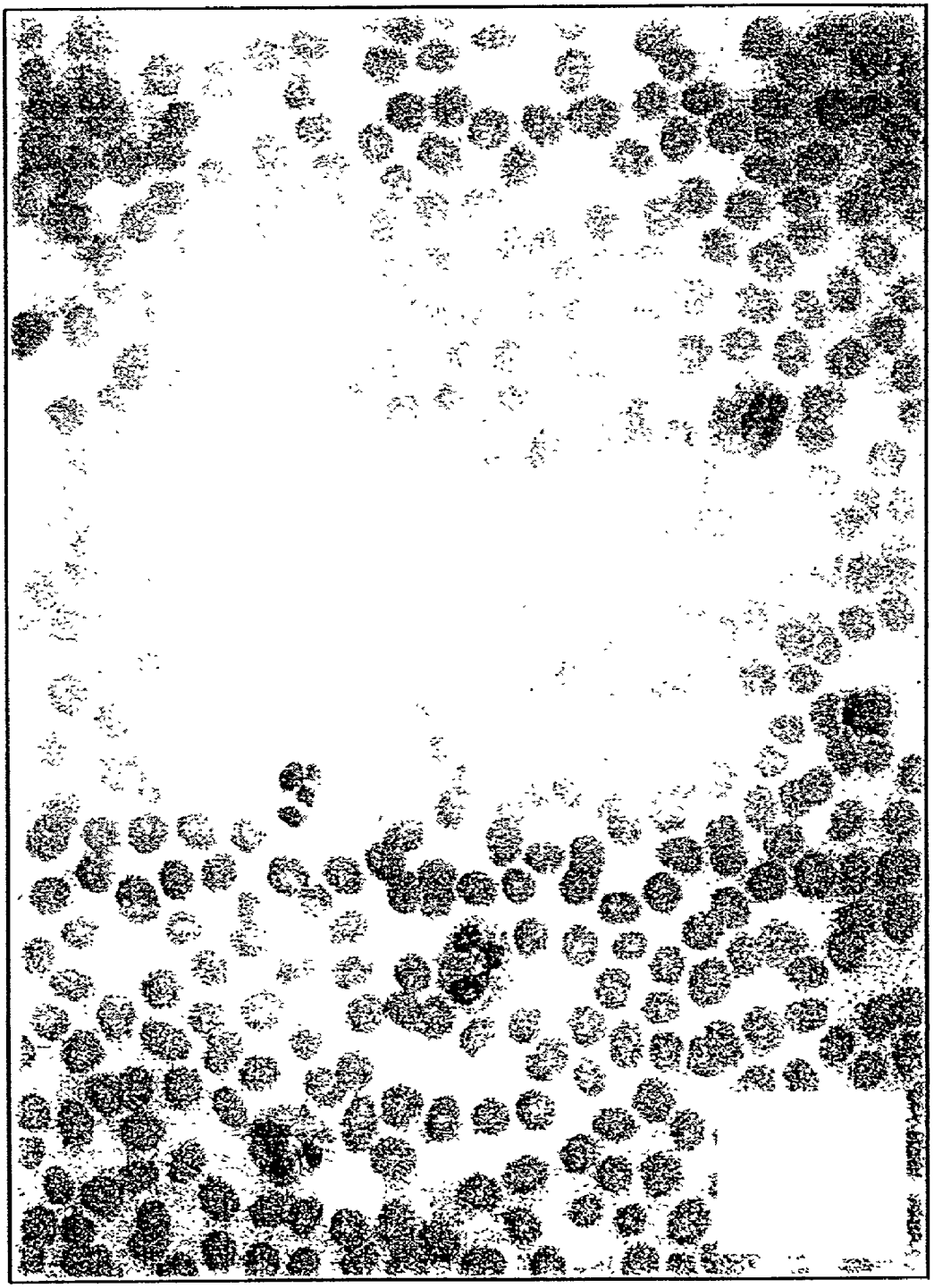
FIG. 6 which is a microscope picture of cells prepared by the method of the present invention.

FIG. 4 is a microscope picture of differentiated B cells before the method of the present invention. FIG. 5 is a microscope picture of undifferentiate cells formed by the retrodifferentiation of the B cells in accordance with the present invention wherein the agent used was a monoclonal antibody to the homologous regions of the β-chain of HLA-DR antigen. Again, the undifferentiated cells are the dark stained clumps of cells. FIG. 6 is a microscope picture of the formation of differentiated granulocyte cells from the same undifferentiated cells of FIG. 5.

FIGS. 4 to 6 therefore visually demonstrate the retrodifferentiation of B cells to undifferentiated stem cells by the method of the present invention followed by commitment of the undifferentiated cells to new differentiated cells being of a different lineage as the original differentiated cells.

The retrodifferentiation of T cells to undifferentiated stem cells by the method of the present invention followed by commitment of the undifferentiated cells to new differentiated cells being of a different lineage as the original differentiated cells was also followed by microscopy.

E. Summary

In short, the examples describe in vitro experiments that reveal extremely interesting findings regarding the ontogeny and development of T and B lymphocytes which can be utilised in the generation of stem cells to affect lymphohaematopoiesis in peripheral blood samples in a matter of hours.

Treatment of peripheral blood samples obtained from patients with B-cell chronic lymphocytic leukaemia's (B-CLL) with high B lymphocyte counts, with monoclonal antibody to the homologous region of the β-chain of class-II antigens gave rise to a marked increase in the relative number of single positive (SP) T-lymphocytes and their progenitors which were double positive for the thymocyte markers CD4 and CD8 antigens and these were coexpressed simultaneously. However, these phenomena were always accompanied by a significant decrease in the relative number of B-lymphocytes. These observations were not noted when the same blood samples were treated with monoclonal antibodies to the homologous region of the α-chain of class-II antigens or to the homologous region of class-I antigens.

Treatment of whole blood obtained from patients with B-cell chronic lymphocytic leukaemia (CLL) with monoclonal antibody to the homologous region of the B chain of the HLA-DR antigen appeared to give rise to T-lymphopoiesis. This event was marked by the appearance of double positive cells coexpressing the CD4 and CD8 markers, the appearance of cells expressing CD34 and the concomitant increase in the number of single positive $CD4^+ CD3^+$ and $CD8^+ CD3^+$ lymphocytes. Furthermore, the immunophenotypic changes that took place in the generation of such cells were identical to those cited for thymocyte development, especially when measured with time.

The percentages of double positive cells (DP) generated at 2 hour incubation time of whole blood with monoclonal antibody to the homologous region of the β-chain of the DR antigen, decreased with time and these events were accompanied by increase in the percentages of single positive $CD4^+ CD3^+$ and $CD8^+ CD3$ cells simultaneously and at later times too. TCR α and β chains were also expressed on these types of cells.

B-lymphocytes were constantly observed to lose markers such as CD19, CD21, CD23, IgM and DR and this coincided with the appearance of $CD34^+$ and $CD34^+ CD2^+$ cells, increases in $CD7^+$ cells, increases in $CD8^+ CD28^+$ and $CD28^+$ cells, increases in $CD25^+$ cells, the appearance of $CD10^+$ and $CD34^+$ cells and $CD34^+$ and $CD19^+$ cells increases in $CD5^+$ cells, and cells expressing low levels of CD45 antigen. These changes were due to treatment of blood with monoclonal antibody to the homologous region of the β-chain of HLA-DR antigen.

The immunophenotypic changes associated with such treatment is consistent with retrodifferentiation and subsequent commitment (i.e. recommitment) of B lymphocytes, because the majority of white blood cells in blood of patients with B-CLL before treatment were B lymphocytes. Furthermore, B-lymphocytes of patients with B-CLL which were induced to become T-lymphocytes following treatment with cyclophosphamide and monoclonal antibody to the β-chain of HLA-DR antigen, were able to revert back to B lymphocytes following prolonged incubation with this treatment.

On analysis of treated samples with monoclonal antibody to the β-chain of HLA-DR antigen, with CD16&56 and CD3 and CD8 and CD3 panels, the relative number of cells expressing these markers steadily increases in increments consistent with those determined with panels such as CD19 and CD3 and DR and CD3. Investigation of the supernatant of treated and untreated samples of patients with HIV infection using nephlometry and immunoelectrophoresis reveals increased levels of IgG indicating that the B-cells must have passed through the plasma cell stage. The increase in the relative number of all above-mentioned cells was also accompanied by the appearance of medium size heavily granulated cells expressing the CD56&16 antigens in extremely high amounts. Other cells which were extremely large and heavily granulated were observed transiently and these were positive for CD34 and double positive for CD4 CD8 markers. Other transient cells were also observed and these were large and granular and positive for the CD3 and CD19 receptors. CD25 which was present on the majority of B-lymphocytes was lost and became expressed by newly formed T-lymphocytes which were always observed to increase in number.

CD28$^+$CD8$^+$ and CD28$^+$ cells appeared after treatment of whole blood of patients with B-CLL with monoclonal antibody to the homologous region of the B chain of the DR antigen. These findings were due to treatment of blood with monoclonal antibody to the homologous region of the β-chain of HLA-DR antigen.

T-lymphopoiesis generated in this manner was also observed in peripheral blood of healthy blood donors, cord blood, bone marrow, patients with various infections including HIV$^+$ individuals and AIDS patients, enriched fractions for B lymphocytes obtained from blood samples of healthy blood donors, IgA deficient patients and other patients with various other conditions. Furthermore, analysis of myeloid markers in treated samples of two patients with B-CLL with monoclonal antibody to the homologous region of the β-chain of the HLA-DR antigen showed a significant increase in the relative number of cells expressing the myeloid markers such as CD13 and CD33. These markers were coexpressed with the CD56 & 16 or the CD7 antigens. However, the relative number of CD7$^+$ cells with T-lymphocyte markers and without myeloid antigens was observed on a separate population of cells. These particular observations were not seen in untreated samples or in samples treated with monoclonal antibodies to class I antigens or the homologous region of the α-chain of HLA-DR antigen (see Charts 2 & 3). These final results suggest that B-lymphocytes once triggered via the β-chain of the HLA-DR antigen are not only able to regress into T-lymphocyte progenitor cells but are also capable of existing into the myeloid and erythroid lineages.

It should be noted that the stem cells that are produced by the method of the present invention may be stem cells of any tissue and are not necessarily limited to lymphohaematopoietic progenitor cells.

Other modifications of the present invention will be apparent to those skilled in the art.

TABLE 1

CLINICAL DIAGNOSIS OF PATIENTS AND EXPERIMENTAL CONDITIONS OF BLOOD SAMPLES INCLUDING COULTER COUNTS (WBC) FOLLOWING AND PRIOR TREATMENT OF BLOOD SPECIMENS WITH VARIOUS MONOCLONAL ANTIBODIES AND OTHER AGENTS

| PATIENT ID | DIAGNOSIS | EXPT COND | WBC/L X10-9 B | WBC/L X10-9 A | % LYMPH B | % LYMPH A | #LYMPH/L 10X-9 B | #LYMPH/L 10X-9 A | AGENT ML/mL |
|---|---|---|---|---|---|---|---|---|---|
| 1 | B-CLL | 12 HR AT 22° C. | 100 | ND | 86.1 | ND | 86.1 | ND | ANTI-B 50 |
| 2 | B-CLL | 2 HR AT 22° C. | 39.1 | 9.6 | 74.4 | 63.3 | 29.9 | 6.1 | ANTI-B 50 |
|   |   | 2 HR AT 22° C. | 39.1 | 37.7 | 74.4 | 75.1 | 29.9 | 28.3 | ANTI-B PE 50 |
| 3 | B-CLL | 6 HR AT 22° C. | 39.5 | 9.3 | 71.9 | 67.2 | 28.3 | 6.2 | ANTI-B 50 |
|   |   | 6 HR AT 22° C. | 39.5 | 37.7 | 71.9 | 72.5 | 28.3 | 27.4 | ANTI-B PE 50 |
| 4 | B-CLL | 24 HR AT 22° C. | 39 | 9.3 | 73 | 66.5 | 28.4 | 6.2 | ANTI-B 50 |
|   |   | 24 HR AT 22° C. | 39 | 36.2 | 73 | 70.4 | 28.4 | 25.5 | ANTI-B PE 50 |
| 5 | B-CLL | 2 HR AT 22° C. |   |   |   |   |   |   | ANTI-B 50 ANTI-A 50 ANTI-I 50 ANTI-B & TOXIC AGENT 25 + 25 |
| 6 | B-CLL | 24 HR AT 22° C. |   |   |   |   |   |   | ANTI-B 50 |
| 7 | B-CLL | 24 HR AT 22° C. | 170 | 128 | 95.4 | 91.1 | 16.9 | 11.6 | ANTI-B 10 |
|   |   |   |   | 178 |   | 94.2 |   | 16.8 | ANTI-I 10 |
|   |   |   |   | 130 |   | 90.4 |   | 11.9 | ANTI-B & TOXIC AGENT 10 + 20 |
| 8 | B-CLL | 24 HR AT 22° C. | 16 | 7 | 81.9 | 51.2 | 14 | 3.0 | ANTI-B 20 |
| 9 | B-CLL | 12 HR AT 22° C. | +++ | 87 | 89.5 | 85.1 | +++ | 76.2 | ANTI-B 30 |
|   |   |   |   |   |   | 85.4 |   |   | ANTI-I |

TABLE 1-continued

CLINICAL DIAGNOSIS OF PATIENTS AND
EXPERIMENTAL CONDITIONS OF BLOOD SAMPLES INCLUDING
COULTER COUNTS (WBC) FOLLOWING AND PRIOR TREATMENT OF BLOOD
SPECIMENS WITH VARIOUS MONOCLONAL ANTIBODIES AND OTHER AGENTS

| PATIENT ID | DIAGNOSIS | EXPT COND | WBC/L X$10^{-9}$ B | WBC/L X$10^{-9}$ A | % LYMPH B | % LYMPH A | #LYMPH/L $10 \times 10^{-9}$ B | #LYMPH/L $10 \times 10^{-9}$ A | AGENT ML/mL |
|---|---|---|---|---|---|---|---|---|---|
|  |  |  |  |  | +++ |  |  | +++ | 30 ANTI-4 |
|  |  |  |  |  |  | 89.4 |  |  | 30 |
|  |  |  |  |  | +++ | 84.9 |  | +++ | ANTI-I + II + 4 |
|  |  |  |  |  |  | 95.4 |  |  | 10 + 10 + 10 |
| 10 | B-CLL | 2 HR AT 22° C. | 19.3 | ND | 86 | ND | 16.7 | ND | ANTI-B 30 ANTI-I 30 |
| 92 | OUT PATIENT | 2 HR AT 22° C. | 5.4 | ND | 74.5 | ND |  | ND | ANTI-B 20 |
| 87 | OUT PATIENT | 2 HR AT 22° C. | 4.8 | ND | 59.3 | ND |  | ND | ANTI-B 20 |
| 91 | OUT PATIENT | 2 HR AT 22° C. | 4.2 | ND | 54.0 | ND |  | ND | ANTI-B 20 |
| 21 | OUT PATIENT | 2 HR AT 22° C. | 3.9 | ND | 47.4 | ND |  | ND | ANTI-B 20 |
| 34 | OUT PATIENT | 2 HR AT 22° C. | 7.2 | ND | 20.0 | ND |  | ND | ANTI-B 20 |
| 36 | CMV INFANT | 4 HR AT 22° C. | 13.4 | ND | 7.3 | ND |  | ND | ANTI-B 20 |
| 93 | HIV + INFANT | 4 HR AT 22° C. | 5.6 | ND | 43.4 | ND |  | ND | ANTI-B 20 |
| BB/ST | 40% BLAST IN BLOOD 6 DAYS OLD | 2 HR AT 22° C. 24 HR AT 22° C. | 60.5 | ND | 20.2 | ND | 12.2 | ND | ANTI-B 50 ANTI-A 50 ANTI-AB 25 + 25 |
| HIV25 | AIDS | 2 HR AT 22° C. | 7.5 | ND | 34.8 | ND | 2.6 | ND | ANTI-B 50 ANTI-A 50 ANTI-AB 25 + 25 |
| 43/BD | B CELL DEFICIENT | 4 HR AT 22° C. |  |  |  |  |  |  | ANTI-B 20 ANTI-I 20 ANTI-4 20 |
| 0B/BD | B CELL DEFICIENT | 4 HR AT 22° C. |  |  |  |  |  |  | ANTI-B 20 ANTI-I 20 ANTI-4 20 |
| HIV + | AIDS | 6 HR AT 22° C. |  |  |  |  |  |  | ANTI-B 20 ANTI-I 20 |
| IgA-D | IgA DEFICIENT | 6 HR AT 22° C. |  |  |  |  |  |  | ANTI-B 20 ANTI-I 20 |

EXPT COND - EXPERIMENTAL CONDITIONS
B: BEFORE
A: AFTER
ANTI-B: monoclonal antibody to the homologous region of the β-chain of HLA-DR anigen
ANTI-A: monoclonal antibody to the homologous region of the α-chain of HLA-DR antigen
ANTI-I: monoclonal antibody to the homologous region of Class I antigens
ANTI-AB: both ANTI-B and ANTI-A added together
ANTI-4: monoclonal antibody to the CD4 antigen
ANTI-I + II + 4: ANTI-I and ANTI-B and ANTI-4 added together
Cytoxic agent: Cyclophophamide
ML/ml: micro litre per ml
L: litre

TABLE 2

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE HOMOLOGOUS REGION OF THE B CHAIN OF THE HLA-DR WITH CD19 AND CD3 MONOCLONAL ANTIBODIES.

| PATIENT | % CD19 + | | % CD3 + | | % CD19 + CD3 + | | % CD3 − CD19 − | | % CD19 + HGCD 3 − FC + | |
|---|---|---|---|---|---|---|---|---|---|---|
| | B | A | B | A | B | A | B | A | B | A |
| 1 | 88 | 40 | 5 | 19 | 1 | 2 | 6 | 26 | 0 | 12 |
| 2 | 73 | 15 | 10 | 33 | 2 | 7 | 15 | 41 | 0 | 5 |
| 3 | 73 | 11 | 11 | 33 | 2 | 2 | 14 | 52 | 0 | 2 |
| 4 | 71 | 13 | 11 | 37 | 2 | 2 | 16 | 47 | 0 | 2 |
| 5 | 85 | 40 | 5 | 16 | 1 | 1 | 6 | 26 | 3 | 18 |
| 6 | 85 | 43 | 5 | 18 | 1 | 1 | 6 | 27 | 3 | 10 |
| 7 | 90 | 72 | 2 | 4 | 0 | 2 | 7 | 8 | 0 | 14 |
| 8 | 62 | 25 | 7 | 13 | 0 | 1 | 29 | 55 | 2 | 6 |
| 9 | 90 | 85 | 2 | 3 | 0 | 0 | 2 | 1 | 1 | 4 |
| 10 | 78 | 50 | 7 | 14 | 0 | 0 | 14 | 26 | 0 | 8 |
| 92 | 12 | 10 | 38 | 49 | 0 | 1 | 49 | 40 | 0 | 0 |
| 91 | 7 | 3 | 35 | 29 | 0 | 1 | 59 | 67 | 0 | 0 |
| 87 | 5 | 3 | 32 | 38 | 1 | 1 | 63 | 58 | 0 | 0 |
| 21 | 1 | 1 | 27 | 29 | 1 | 0 | 71 | 70 | 0 | 0 |
| 34 | 1 | 1 | 13 | 13 | 0 | 2 | 86 | 84 | 0 | 0 |
| 39 | 10 | 6 | 23 | 25 | 0 | 0 | 67 | 69 | 0 | 0 |
| 93 | 6 | 3 | 26 | 27 | 1 | 1 | 68 | 70 | 0 | 0 |
| BB/ST | 1 | 1 | 12 | 13 | 0 | 0 | 87 | 86 | 0 | 0 |
| HIV25 | 7 | 2 | 26 | 27 | 0 | 0 | 68 | 67 | 0 | 0 |
| 43/BD | 0 | 0 | 40 | 42 | 0 | 1 | 58 | 54 | 0 | 0 |
| 04/BD | 0 | 0 | 49 | 41 | 0 | 3 | 43 | 41 | 0 | 0 |
| HIV + | 1 | 1 | 10 | 14 | 0 | 0 | 89 | 87 | 0 | 0 |
| IgA/D | 10 | 1 | 21 | 25 | 2 | 3 | 67 | 71 | 0 | 0 |

B: before treatment
A: after treatment

TABLE 3

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE B CHAIN OF THE HOMOLOGOUS REGION OF THE HLA-DR WITH MONOCLONAL ANTIBODIES TO CD4 AND CD8.

| PATIENT | % CD8 + | | % CD4 + | | % CD4 + CD8 + | | % CD4 − CD8 − | | CD4 + LOW | |
|---|---|---|---|---|---|---|---|---|---|---|
| | B | A | B | A | B | A | B | A | B | A |
| 1 | 2.8 | 16 | 2.9 | 11.4 | 0 | 3.2 | 93.1 | 67.6 | 0 | 0 |
| 2 | 6.2 | 13.2 | 9.1 | 24.3 | 0 | 9.4 | 78.7 | 46 | 5.8 | 6.3 |
| 3 | 7.2 | 13.1 | 7.4 | 23.9 | 0 | 8.2 | 78.8 | 48.1 | 6.3 | 6.6 |
| 4 | 10.1 | 24.2 | 7.6 | 24.9 | 0.3 | 2.8 | 77.5 | 42 | 4.6 | 5 |
| 5 | 2.9 | 16.2 | 1.8 | 7.6 | 0 | 2 | 95 | 62.3 | 0 | 0 |
| 6 | ND | 12 | ND | 8.1 | ND | 1.7 | ND | 75.7 | ND | 0 |
| 7 | 1.9 | 2.6 | 1.9 | 2.8 | 0 | 0 | 95.8 | 94.3 | 0 | 0 |
| 8 | 3.2 | 7 | 3.9 | 6.9 | 0.1 | 2 | 87.3 | 79.8 | 4.3 | 6 |
| 9 | 2.8 | 2.9 | 3 | 3 | 0 | 0 | 94 | 94.1 | 0 | 0 |
| 10 | 5.7 | 9.4 | 4.7 | 9.1 | 0.6 | 0.8 | 88.7 | 79.2 | 0 | 0 |
| 92 | 21 | 19 | 21.6 | 21 | 0.8 | 1.9 | 50.5 | 52.5 | 5.3 | 4.8 |
| 91 | 15.4 | 18.1 | 13.6 | 17.9 | 6.2 | 2.6 | 57 | 57.3 | 7.3 | 3.5 |
| 87 | 16.8 | 21.8 | 13.4 | 20.4 | 2.9 | 2.6 | 59.5 | 48.9 | 7 | 5.6 |
| 21 | 16 | 24.1 | 9.1 | 15.2 | 1 | 2.6 | 69.6 | 53.2 | 3.7 | 4.2 |
| 34 | 9.4 | 11.9 | 5.7 | 4.9 | 2 | 3.3 | 67.6 | 65.3 | 14.4 | 14.5 |
| 39 | 12.1 | 12.6 | 13.1 | 14.6 | 0.4 | 1.3 | 62.3 | 66.7 | 11.9 | 4.3 |
| 93 | 18.9 | 20.3 | 9.7 | 10.3 | 1.8 | 1.4 | 65.5 | 65.9 | 3.4 | 1.8 |
| BB/ST | 6.3 | 13 | 5.7 | 7.3 | 2.2 | 1.1 | 34.7 | 70.3 | 50.3 | 7.6 |
| HIV25 | 24.1 | 24.9 | 0.8 | 1.1 | 1.3 | 5 | 70.2 | 69.3 | 2.9 | 3.8 |

TABLE 4

IMMUNOPHENOTYPING OF PATIENTS WITH B-CLL AND OTHER CONDITIONS BEFORE AND AFTER TREATMENT OF SAMPLES WITH MONOCLONAL ANTIBODY TO THE B CHAIN OF THE HLA-DR WITH MONOCLONAL ANTIBODIES TO CD3 AND DR

| PATIENT | DR + B | DR + A | CD + B | CD + A | CD + DR + B | CD + DR + A | DR − CD3 − B | DR − CD3 − A | DR + hcD3 − B | DR + hcD3 − A |
|---|---|---|---|---|---|---|---|---|---|---|
| 1 | 87 | 45.5 | 3.5 | 20.8 | 2.5 | 4.2 | 6.9 | 21.6 | 0 | 7.6 |
| 2 | 76.2 | 19.4 | 9.6 | 29.2 | 3.9 | 8.7 | 10.3 | 36.8 | 0 | 5.5 |
| 3 | 77.7 | 18.3 | 8.4 | 29.4 | 4.1 | 8.8 | 9.6 | 38.1 | 0 | 4.7 |
| 4 | 76.8 | 19.2 | 7.6 | 29.5 | 6.2 | 10.5 | 9.1 | 37.2 | 0 | 3.3 |
| 5 | ND | 47.1 | ND | 11.5 | ND | 9.9 | ND | 22.4 | ND | 7.3 |
| 6 | ND | | | | | | | | | |
| 7 | 91.4 | 85.8 | 2.4 | 2.5 | 0.7 | 0.7 | 5.1 | 4.2 | 0 | 6.3 |
| 8 | 61.8 | 28.9 | 6.5 | 11.2 | 2 | 3.3 | 28.6 | 54.6 | 0 | 1.5 |
| 9 | ND | | | | | | | | | |
| 10 | 82.6 | 44.7 | 4.3 | 9.8 | 3.3 | 5 | 9.8 | 22.2 | 0 | 17.9 |
| 92 | 23.8 | 14.1 | 39.3 | 41.9 | 4.5 | 3.5 | 32.4 | 40.5 | 0 | 0 |
| 91 | 13.3 | 7.9 | 29.6 | 32.5 | 3.4 | 2.9 | 53.4 | 56.5 | 0 | 0 |
| 87 | 14.8 | 12.2 | 28.4 | 34.1 | 5.5 | 6.6 | 51.1 | 46.5 | 0 | 0 |
| 21 | ND | | | | | | | | | |
| 34 | 11.9 | 12.9 | 10.4 | 13.7 | 0.8 | 0.6 | 76.7 | 72.8 | 0 | 0 |
| 39 | 25.6 | 13.7 | 24.6 | 25.2 | 3 | 2.8 | 46.5 | 25.2 | 0 | 0 |
| 93 | 13.3 | 8.9 | 18.4 | 18.9 | 9.9 | 10.1 | 58.2 | 61.7 | 0 | 0 |
| BB/ST | 44.2 | 32.5 | 11.7 | 12.2 | 0.8 | 0.8 | 43 | 49.4 | 0 | 4.6 |

TABLE 5

IMMUNOPHENOTYPING OF PATIENTS WITH B-CLL AND OTHER CONDITIONS BEFORE AND AFTER TREATMENT OF BLOOD SAMPLES WITH MONOCLONAL ANTIBODY TO THE HOMOLOGOUS REGION OF THE B CHAIN OF THE HLA-DR WITH MONOCLONAL ANTIBODIES TO CD16 + 56 AND CD3.

| PATIENTS | CD56 + & 16 B | CD56 + & 16 A | CD3 + B | CD3 + A | CD56 + & 16 + CD3 + B | CD56 + & 16 + CD3 + A | CD56 + & 16 − CD3 B | CD56 + & 16 − CD3 A |
|---|---|---|---|---|---|---|---|---|
| 1 | 2 | 4.3 | 5.7 | 19.7 | 0.7 | 1.7 | 91.3 | 73 |
| 2 | 11.5 | 38.9 | 12.4 | 32.6 | 1 | 6.6 | 74.5 | 21 |
| 3 | 12 | 36.2 | 12.1 | 34.5 | 0.7 | 6 | 75.5 | 23 |
| 4 | 12.2 | 32.6 | 12.4 | 39.6 | 0.5 | 5 | 74.7 | 22.2 |
| 5 | ND | 13.1 | ND | 9.4 | ND | 2.6 | ND | 73.5 |
| 6 | ND | | | | | | | |
| 7 | 0.8 | 0.8 | 2.8 | 2.4 | 0.3 | 0.2 | 96.2 | 96.4 |
| 8 | 24.8 | 52 | 5.4 | 12.4 | 0.9 | 4.1 | 68.3 | 31.1 |
| 9 | ND | | | | | | | |
| 10 | 1.1 | 1.3 | 6.1 | 13.7 | 2.1 | 2.5 | 90.5 | 82.4 |
| 92 | 23.8 | 34.5 | 44.3 | 44.8 | 2 | 1.5 | 29.2 | 18.6 |
| 91 | 4.6 | 3.9 | 28.8 | 29.4 | 3 | 3.2 | 63.3 | 63.3 |
| 87 | 47.9 | 46.4 | 28.8 | 36.5 | 5.8 | 3.7 | 16.9 | 13 |
| 21 | 9.4 | 9.4 | 19.7 | 23.6 | 4.2 | 6.7 | 66 | 59.5 |
| 34 | 21.5 | 12.8 | 11.4 | 13.7 | 1.8 | 0.6 | 64.6 | 72.8 |
| 39 | 7 | 2.7 | 23.4 | 26.1 | 1.1 | 0.1 | 68.2 | 71 |
| 93 | 55.8 | 54.9 | 26.2 | 26.3 | 1.7 | 2 | 16.1 | 16.8 |
| BB/ST | 28.8 | 29.9 | 12 | 14.3 | 0.8 | 1.8 | 49.4 | 53.6 |

TABLE 6

IMMUNOPHENTYPING OF PATIENTS WITH B-CLL AND OTHER CONDITIONS BEFORE AND AFTER OF TREATMENT OF BLOOD WITH MONOCLONAL ANTIBODY TO THE HOMOLOGOUS REGION OF THE B CHAIN OF THE HLA-DR WITH MONOCLONAL ANTIBODIES TO CD45 AND CD14.

| PATIENTS | CD45 + H B | CD45 + H A | CD45 + L B | CD45 + L A | CD45 + CD14 + B | CD45 + CD14 + A |
|---|---|---|---|---|---|---|
| 1 | 90.5 | 70.1 | 7.5 | 21.9 | 0.8 | 3.3 |
| 2 | 85.8 | 52.2 | 8.8 | 38.3 | 5.3 | 9.5 |
| 3 | 84.3 | 52.2 | 9.9 | 33.8 | 5.1 | 13.2 |
| 4 | 91.5 | 79.2 | 2.1 | 7 | 5.7 | 10.8 |
| 5 | 63.1 | 84.6 | 34.9 | 9.4 | 0.5 | 3.6 |
| 6 | ND | | | | | |
| 7 | 52.8 | 85.2 | 45.6 | 13.9 | 0.5 | 0.6 |
| 8 | 71.1 | 55 | 71.1 | 34.5 | 5.3 | 8.7 |
| 9 | SEE | | | | | |
| 10 | 79.7 | 47.3 | 16.3 | 48 | 2.1 | 1.9 |
| 92 | 61.7 | 64.7 | 27.4 | 26.6 | 5.9 | 3.6 |
| 91 | 49.4 | 49.2 | 40.4 | 44.3 | 6.5 | 3.2 |
| 87 | 52.4 | 61.5 | 36.1 | 28.7 | 7 | 6.5 |
| 21 | 45.8 | 43.3 | 44.3 | 47.6 | 6.2 | 6.3 |
| 34 | 24.4 | 24.6 | 54.8 | 59.6 | 13.3 | 9.7 |
| 39 | 48.7 | 46.3 | 30.5 | 42.1 | 14.5 | 8.8 |
| 93 | SEE | | | | | |
| HIV + | 22.6 | 26.9 | 66.8 | 63.5 | 6.8 | 6.7 |
| IgA/D | 47.4 | 59.8 | 41.9 | 33.3 | 5.9 | 4.1 |

TABLE 7

IMMUNOPHENOTYPING OF PATIENT WITH B-CLL AND OTHER CONDITIONS BEFORE AND AFTER TREATMENT OF BLOOD WITH MONOCLONAL ANTIBODIES TO THE HOMOLOGOUS REGION OF THE B-CHAIN OF THE HLA-DR WITH MONOCLONAL ANTIBODIES TO CD8 AND CD3.

| PATIENTS | CD8 + B | CD8 + A | CD3 + B | CD3 + A | CD8 + CD3 + B | CD8 + CD3 + A | CD8 − CD3 − B | CD8 − CD3 − A |
|---|---|---|---|---|---|---|---|---|
| 2 | 0.6 | 1.3 | 7.5 | 19.3 | 4.2 | 19.3 | 87.7 | 63.8 |
| 3 | 1.1 | 1.4 | 8.3 | 20.3 | 5.6 | 18.4 | 84.8 | 59.8 |
| 4 | 3.5 | 2.9 | 8.3 | 27 | 3.9 | 16.6 | 84.2 | 53.1 |

TABLE 7-continued

IMMUNOPHENOTYPING OF PATIENT WITH
B-CLL AND OTHER CONDITIONS BEFORE AND AFTER
TREATMENT OF BLOOD WITH MONOCLONAL ANTIBODIES
TO THE HOMOLOGOUS REGION OF THE B-CHAIN OF THE
HLA-DR WITH MONOCLONAL ANTIBODIES TO CD8 AND CD3.

| | CD8 + | | CD3 + | | CD8 + CD3 + | | CD8 − CD3 − | |
|---|---|---|---|---|---|---|---|---|
| PATIENTS | B | A | B | A | B | A | B | A |
| 92 | 3.5 | 1.9 | 27.6 | 25.2 | 18.4 | 19 | 50.3 | 52.8 |
| 91 | 4 | 3.1 | 18.2 | 19 | 14.1 | 12.6 | 63.6 | 65.3 |
| 87 | 5.7 | 3.9 | 19.9 | 23.6 | 15.4 | 17.4 | 58.8 | 55 |
| 21 | 4.8 | 7.4 | 16.3 | 17.3 | 13.7 | 13 | 65.2 | 62 |
| 34 | 3 | 3.6 | 5.2 | 6.7 | 7.6 | 7.5 | 84.1 | 82.3 |

TABLE 8

IMMUNOPHENOTYPING
OF A PATIENT WITH B-CLL WITH TIME
AFTER TREATMENT OF BLOOD WITH PE CONJUGATED
MONOCLONAL ANTIBODY TO THE HOMOLOGOUS
REGION OF THE B-CHAIN OF THE HLA-DR MEASURE
WITH MONOCLONAL ANTIBODIES TO CD45 AND CD14.

| TIME | DR + CD45 + CD14 + r | CD45 + L | CD45 + H |
|---|---|---|---|
| 2 HR | 81.7 | 8.2 | 8.2 |
| 6 HR | 80.7 | 8.1 | 10.6 |
| 24 HR | 79 | 1.1 | 18.4 |

TABLE 9

IMMUNOPHENOTYPING OF
A PATIENT WITH B-CLL WITH TIME
AFTER TREATMENT OF BLOOD WITH PE CONJUGATED
MONOCLONAL ANTIBODY TO THE HOMOLOGOUS
REGION OF THE B-CHAIN OF THE HLA-DR MEASURED
WITH MONOCLONAL ANTIBODIES TO CD19 AND CD3.

| TIME | CD19 + DR + r | CD3 + | CD3 + DR + | CD19 − CD3 − DR − |
|---|---|---|---|---|
| 2 HR | 87.4 | 10.1 | 1.8 | 10.7 |
| 6 HR | 75.5 | 10.4 | 3.1 | 10.7 |
| 24 HR | 74 | 11.7 | 2.9 | 11 |

TABLE 10

IMMUNOPHENOTYPING OF
A PATIENT WITH B-CLL WITH TIME
AFTER TREATMENT OF BLOOD WITH PE CONJUGATED
MONOCLONAL ANTIBODY TO THE HOMOLOGOUS
REGION OF THE B-CHAIN OF THE HLA-DR MEASURED
WITH MONOCLONAL ANTIBODIES TO CD4 AND CD8.

| TIME | CD8 + & DR + r | CD4 + | CD4 + & CD8 + & DR + r | CD4 + DR + | CD4 − CD8 − DR− |
|---|---|---|---|---|---|
| 2 HR | 77.6 | 6.8 | 5.4 | 1.3 | 8.8 |
| 6 HR | 75.8 | 6.7 | 6.4 | 1.8 | 9.3 |
| 24 HR | 77 | 6.4 | 4.8 | 1.9 | 11 |

TABLE 11

IMMUNOPHENOTYPING OF A PATIENT WITH B-CLL WITH
TIME AFTER TREATMENT OF BLOOD WITH PE CONJUGATED
MONOCLONAL ANTIBODY TO THE HOMOLOGOUS REGION
OF THE B-CHAIN OF THE HLA-DR MEASURED WITH
MONOCLONAL ANTIBODIES TO CD3 AND DR.

| TIME | DR + | CD3 + | CD3 + DR + | CD3 + DR − |
|---|---|---|---|---|
| 2 HR | 75 | 9.5 | 4.2 | 10.9 |
| 6 HR | 74.8 | 8.8 | 4.8 | 10.9 |
| 24 HR | ND | ND | ND | ND |

TABLE 12

IMMUNOPHENOTYPING OF A PATIENT WITH B-CLL WITH
TIME AFTER TREATMENT OF BLOOD WITH PE CONJUGATED
MONOCLONAL ANTIBODY TO THE HOMOLOGOUS REGION
OF THE B-CHAIN OF THE HLA-DR MEASURED WITH
MONOCLONAL ANTIBODIES TO CD16 & 56 AND CD3.

| TIME | CD56 + & 16 + DR + r | CD3 + | CD56 + CD16 + & CD3 + DR + r | CD56 − CD16 − & CD16 − DR − |
|---|---|---|---|---|
| 2 HR | 82.5 | 9.5 | 4.1 | 3.5 |
| 6 HR | 84.3 | 7.5 | 4.1 | 3.3 |
| 24 HR | ND | ND | ND | ND |

TABLE 13

IMMUNOPHENOTYPING OF A PATIENT WITH B-CLL WITH
TIME AFTER TREATMENT OF BLOOD WITH PE CONJUGATED
MONOCLONAL ANTIBODY TO THE HOMOLOGOUS REGION
OF THE B-CHAIN OF THE HLA-DR MEASURED WITH
MONOCLONAL ANTIBODIES TO CD8 AND CD3.

| TIME | CD8 + DR + | CD3 + | CD8 + CD + 3 & DR + r | CD8 − CD3 − DR − |
|---|---|---|---|---|
| 2 HR | 76.2 | 6.6 | 6.7 | 10.6 |
| 6 HR | 76.5 | 6.2 | 6.2 | 10.3 |

TABLE 14

IMMUNOPHENOTYPING OF PATIENTS WITH B-CLL BEFORE AND AFTER TREATMENT OF BLOOD WITH MONOCLONAL ANTIBODIES TO THE HOMOLOGOUS REGION OF THE A-CHAIN OF THE HLA-DR, THE HOMOLOGOUS REGION OF THE B-CHAIN OF THE HLA-DR, THE TWO MONOCLONAL TOGETHER, MONOCLONAL TO THE HOMOLOGOUS REGION OF THE B-CHAIN PLUS CYCLOPHOSPHOAMIDE AND THE HOMOLOGOUS REGION OF CLASS I ANTIGENS MEASURED WITH TIME.

| | CD19 + | | | | | CD3 + | | | | | CD19 + CD3 + | | | | | CD19 − D3 − | | | | |
|---|---|---|---|---|---|---|---|---|---|---|---|---|---|---|---|---|---|---|---|---|
| ID | B | AA | AB | ABC | AI | B | AA | AB | ABC | AI | B | AA | AB | ABC | AI | B | AA | AB | ABC | AI |
| 5/6 2H | 86 | 91 | 54 | 40 | 89 | 5 | 4 | 16 | 23 | 5 | 1 | 1 | 3 | 2 | 1 | 6 | 4 | 27 | 33 | 5 |
| 24 10 | N | 88 | 51 | 60 | 86 | N | 4 | 18 | 10 | 4 | N | 2 | 1 | 2 | 3 | N | 4 | 29 | 28 | 7 |
| 2H 09 | 77 | N | 59 | N | 80 | 7 | N | 13 | N | 7 | 1 | N | 1 | N | 0 | 14 | N | 26 | N | 12 |
| 24 43/BD | 8 | N | N | N | 6 | 32 | N | N | N | 38 | 1 | N | N | N | 1 | 59 | N | N | N | 56 |
| 6H 04/BD | 0 | N | 0 | 0 | 0 | 40 | N | 42 | 43 | 49 | 0 | N | 1 | 0 | 1 | 58 | N | 54 | 54 | 47 |
| 6H HIV+ | 0 | N | 0 | 0 | 0 | 49 | N | 41 | 45 | 46 | 0 | N | 3 | 1 | 3 | 43 | N | 42 | 44 | 41 |
| 6H IgA/D | 1 | N | 0 | N | 1 | 10 | N | 14 | N | 12 | 0 | N | 0 | N | 0 | 89 | N | 86 | N | 87 |
| 6H | 10 | N | 1 | N | 12 | 21 | N | 25 | N | 20 | 2 | N | 1 | N | 3 | 67 | N | 71 | N | 68 |

B = Before:
A = After:
AB = after addition to antibody to beta chain:
AA = after addition of antibody to alpha chain:
ABC = after addition of antibody to either alpha or beta chain and cycloposphoamide:
AI = after addition of antibody to Class I.

TABLE 15

CD8 AND CD4

| | CD8 + | | | | | CD4 + | | | | | CD4 + CD8 + | | | | | CD4 − CD8 − | | | | |
|---|---|---|---|---|---|---|---|---|---|---|---|---|---|---|---|---|---|---|---|---|
| ID | B | AA | AB | ABC | AI | B | AA | AB | ABC | AI | B | AA | AB | ABC | AI | B | AA | AB | ABC | AI |
| 5/6 2H | 3 | 2 | 14 | 10 | 4 | 2 | 2 | 8 | 8 | 3 | 0 | 0 | 3 | 2 | 1 | 95 | 94 | 74 | 79 | 93 |
| 24 10 | N | 3 | 9 | 4 | 4 | N | 3 | 8 | 4 | 3 | N | 0 | 2 | 2 | 0 | N | 94 | 81 | 90 | 93 |
| 2H 09 | 3 | N | 7 | N | 4 | 4 | N | 7 | N | 3 | 1 | N | 2 | N | 1 | 91 | N | 83 | N | 92 |
| 24 | 10 | N | N | N | 15 | 21 | N | N | N | 38 | 2 | N | N | N | 2 | 61 | N | N | N | 53 |

TABLE 16

CD3 AND DR

| | DR + | | | | | CD3 + | | | | | CD3 + DR + | | | | | CD3 − DR − | | | | |
|---|---|---|---|---|---|---|---|---|---|---|---|---|---|---|---|---|---|---|---|---|
| ID | B | AA | AB | ABC | AI | B | AA | AB | ABC | AI | B | AA | AB | ABC | AI | B | AA | AB | ABC | AI |
| 5/6 2H | N | 90 | 54 | N | 87 | N | 4 | 12 | N | 4 | N | 2 | 10 | N | 3 | N | 5 | 22 | N | 5 |
| 10 2H | 83 | N | 63 | N | 81 | 4 | N | 8 | N | 4 | 4 | N | 7 | N | 4 | 9 | N | 23 | N | 12 |
| 09 24 | 14 | N | N | N | 13 | 30 | N | N | N | 36 | 3 | N | N | N | 3 | 51 | N | N | N | 47 |

TABLE 17

CD16 & 56 AND CD3

| | CD56 + & 16 + | | | | | CD3 + | | | | | CD56 + & 16 + CD3 + | | | | | CD56 − & 16 − CD3 − | | | | |
|---|---|---|---|---|---|---|---|---|---|---|---|---|---|---|---|---|---|---|---|---|
| ID | B | AA | AB BC | A | AI | B | AA | AB BC | A | AI | B | AA | AB BC | A | AI | B | AA | AB BC | A | AI |
| 5/6 2H 10 | N | 0 | 13 | N | 4 | N | 5 | 9 | N | 5 | N | 1 | 3 | N | 1 | N | 94 | 74 | N | 90 |
| 2H 09 | 0 | N | 1 | N | 1 | 6 | N | 14 | N | 6 | 1 | N | 2 | N | 1 | 92 | N | 65 | N | 92 |
| 24 | 42 | N | N | N | 41 | 36 | N | N | N | 38 | 2 | N | N | N | 2 | 20 | N | N | N | 19 |

TABLE 18

CD45 AND CD14

| | CD45 + L | | | | | CD45 + M | | | | | CD45 + H | | | | | CD45 + CD14 + | | | | |
|---|---|---|---|---|---|---|---|---|---|---|---|---|---|---|---|---|---|---|---|---|
| ID | B | AA | AB BC | A | AI | B | AA | AB BC | A | AI | B | AA | AB BC | A | AI | B | AA | AB BC | A | AI |
| 5/6 2H 10 | 0 | 0 | 5 | 10 | 0 | 44 | 43 | 50 | 50 | 32 | 55 | 43 | 50 | 31 | 67 | 1 | 1 | 1 | 2 | 0 |
| 2H 09 | 0 | N | 0 | N | 0 | 43 | N | 54 | N | 35 | 54 | N | 42 | N | 62 | 1 | N | 1 | N | 0 |
| 24 HIV+ | 2 | N | N | N | 1 | 18 | N | N | N | 16 | 71 | N | N | N | 76 | 7 | N | N | N | 5 |
| 6H IgA/D | 4 | N | 3 | N | 6 | 63 | N | 61 | N | 41 | 23 | N | 27 | N | 40 | 7 | N | 7 | N | 7 |
| 6H | 2 | N | 2 | N | 4 | 40 | N | 31 | N | 44 | 47 | N | 60 | N | 44 | 6 | N | 4 | N | 6 |

TABLE 19

CD8 AND CD28

| | CD8 + | | | | | CD28 + | | | | | CD8 + CD28 + | | | | | CD8 − CD28 − | | | | |
|---|---|---|---|---|---|---|---|---|---|---|---|---|---|---|---|---|---|---|---|---|
| ID | B | AA | AB BC | A | AI | B | AA | AB BC | A | AI | B | AA | AB BC | A | AI | B | AA | AB BC | A | AI |
| 5/6 2H 8 | N | 3 | 6 | N | 3 | N | 1 | 4 | N | 2 | N | 1 | 4 | N | 1 | N | 95 | 86 | N | 94 |
| 2H | 4 | N | 6 | N | N | 3 | N | 5 | N | N | 1 | N | 3 | N | N | 92 | N | 86 | N | N |

TABLE 20

CD34 AND CD2

| | CD34 + | | | | | CD2 + | | | | | CD34 + CD2 + | | | | | CD34 − CD2 − | | | | |
|---|---|---|---|---|---|---|---|---|---|---|---|---|---|---|---|---|---|---|---|---|
| ID | B | AA | AB BC | A | AI | B | AA | AB BC | A | AI | B | AA | AB BC | A | AI | B | AA | AB BC | A | AI |
| 5/6 2H | N | 1 | 34 | N | N | N | 6 | 13 | N | N | N | 3 | 30 | N | N | N | 90 | 21 | N | N |
| 24 HIV− | N | 1 | 6 | 9 | N | N | 7 | 23 | 4 | N | N | 3 | 33 | 43 | N | N | 87 | 34 | 34 | N |
| 2H BB/ST | 2 | 1 | 12 | 13 | N | 20 | 21 | 21 | 12 | N | 4 | 5 | 9 | 14 | N | 73 | 73 | 64 | 60 | N |

TABLE 20-continued

CD34 AND CD2

| | CD34 + | | | | CD2 + | | | | CD34 + CD2 + | | | | CD34 − CD2 − | | | |
|---|---|---|---|---|---|---|---|---|---|---|---|---|---|---|---|---|
| 2H | 26 | 23 | 33 | 14 | N | 15 | 14 | 15 | 15 | N | 31 | 30 | 23 | 36 | N | 27 | 2 | 32 | 28 | 35 | N |
| 24 | N | 11 | 29 | 11 | N | N | 13 | 12 | 9 | N | N | 27 | 9 | 18 | N | N | 48 | 49 | 61 | N |

CHART 1

IMMUNOPHENOTYPIC CHANGES OF UNTREATED AND TREATED BLOOD SAMPLE OF PATIENT (2, 3 & 4) WITH MONOCLONAL ANTIBODY TO THE HOMOLOGOUS REGION OF THE β-CHAIN OF HLA-DR ANTIGEN MEASURED WITH TIME.

| WITHOUT | WITH | FL1 | FL2 | TIME |
|---|---|---|---|---|
| NOTHING001 | WITH002 | CD45 | CD14 | 2 HR |
| NO001 | WE002 | CD45 | CD14 | 6 HR |
| 001001 | 002002 | CD45 | CD14 | 24 HR |
| NOTHING003 | WITH004 | CD3 | CD19 | 2 HR |
| NO003 | WE004 | CD3 | CD19 | 6 HR |
| 001003 | 002004 | CD3 | CD19 | 24 HR |
| NOTHING004 | WITH005 | CD4 | CD8 | 2 HR |
| NO004 | WE005 | CD4 | CD8 | 6 HR |
| 001004 | 002005 | CD4 | CD8 | 24 HR |
| NOTHING005 | WITH006 | CD3 | DR | 2 HR |
| NO005 | WE006 | CD3 | DR | 6 HR |
| 001005 | 002006 | CD3 | DR | 24 HR |
| NOTHING006 | WITH007 | CD3 | CD56&16 | 2 HR |
| NO006 | WE007 | CD3 | CD56&16 | 6 HR |
| 001006 | 002007 | CD3 | CD56&16 | 24 HR |
| N003 | W004 | CD3 | CD8 | 2 HR |
| NO007 | WE008 | CD3 | CD8 | 6 HR |
| 001007 | 002008 | CD3 | CD8 | 24 HR |

CHART 1A

IMMUNOPHENOTYPIC CHANGES OF UNTREATED AND TREATED BLOOD SAMPLE OF PATIENT (2, 3, 4) WITH MONOCLONAL ANTIBODY TO THE HOMOLOGOUS REGION OF THE β-CHAIN OF HLA-DR ANTIGEN CONJUGATED TO PE MEASURED WITH TIME.

| ID | FL1 | FL2 | TIME |
|---|---|---|---|
| WL003 | CD45 | CD14 | 2 HR |
| WEL003 | CD45 | CD14 | 6 HR |
| 003003 | CD45 | CD14 | 24 HR |
| WL005 | CD3 | CD19 | 2 HR |
| WEL005 | CD3 | CD19 | 6 HR |
| 003005 | CD3 | CD19 | 24 HR |
| WL006 | CD4 | CD8 | 2 HR |
| WEL006 | CD4 | CD8 | 6 HR |
| 003006 | CD4 | CD8 | 24 HR |
| WL007 | CD3 | DR | 2 HR |
| WEL 007 | CD3 | DR | 6 HR |
| WL008 | CD3 | CD65&16 | 2 HR |
| WEL 008 | CD3 | CD56&16 | 6 HR |
| WL005 | CD3 | CD8 | 2 HR |
| WEL009 | CD3 | CD8 | 6 HR |

CHART 2

IMMUNOPHENOTYPIC CHANGES OF UNTREATED AND TREATED BLOOD OF PATIENT (1) WITH MONOCLONAL ANTIBODY TO THE HOMOLOGOUS REGION OF THE β-CHAIN OF HLA-DR ANTIGEN. THIS ANTIBODY AND CYCLOPHOSPHAMIDE. MONOCLONAL ANTIBODY TO THE HOMOLOGOUS REGION OF THE α-CHAIN OF HLA-DR ANTIGEN AND MONOCLONAL ANTIBODY TO THE HOMOLOGOUS REGION OF CLASS I ANTIGEN MEASURED WITH TIME.

| WITH | WITHOUT | FL1 | FL2 | TIME |
|---|---|---|---|---|
| | NA001 | CD45 | CD14 | 2 HR |
| A2B001:AB | | CD45 | CD14 | 2 HR |
| A2A:AA | | CD45 | CD14 | 2 HR |
| DNAA001:ABC | | CD45 | CD14 | 2 HR |
| A1001:AI | | CD45 | CD14 | 2 HR |
| | NC001 | CD3 | CD19 | 2 HR |
| C2B001.AB | | CD3 | CD19 | 2 HR |
| C2A001:AA | | CD3 | CD19 | 2 HR |
| DNAC001:ABC | | CD3 | CD19 | 2 HR |
| C1001:AI | | CD3 | CD19 | 2 HR |
| A124H001:AI | | CD3 | CD19 | 24 HR |
| A2B24H001:AB | | CD3 | CD19 | 24 HR |
| A2A24H001:AA | | CD3 | CD19 | 24 HR |
| A2BX24H001:ABC | | CD3 | CD19 | 24 HR |
| | ND001 | CD4 | CD8 | 2 HR |
| D2B001:AB | | CD4 | CD8 | 2 HR |
| D2A001:AA | | CD4 | CD8 | 2 HR |
| DNAD001:ABC | | CD4 | CD8 | 2 HR |
| D1001:AI | | CD4 | CD8 | 2 HR |
| D124H001:AI | | CD4 | CD8 | 24 HR |
| D2BX24H001:ABC | | CD4 | CD8 | 24 HR |
| D2B001:AB | | CD4 | CD8 | 24 HR |
| D2A001:AA | | CD4 | CD8 | 24 HR |
| E1001:AI | | CD3 | DR | 2 HR |
| E2B001:AB | | CD3 | DR | 2 HR |
| E2A001:AA | | CD3 | DR | 2 HR |
| F1001:AI | | CD3 | CD56&16 | 2 HR |
| F2B001:AB | | CD3 | CD56&16 | 2 HR |
| F2A001:AA | | CD3 | CD56&16 | 2 HR |
| G1001:AI | | CD28 | CD8 | 2 HR |
| G2A001:AA | | CD28 | CD8 | 2 HR |
| G2B001:AB | | CD28 | CD8 | 2 HR |
| H1001:AI | | CD7 | CD33&13 | 2 HR |
| H2A001:AA | | CD7 | CD33&13 | 2 HR |
| H2B001:AB | | CD7 | CD33&13 | 2 HR |
| I2A001:AA | | CD21 | CD5 | 2 HR |
| I2B001:AB | | CD21 | CD5 | 2 HR |
| J2A001:AA | | CD34 | CD2 | 2 HR |
| J2B001:AB | | CD34 | CD2 | 2 HR |
| B2A24H001:AA | | CD34 | CD2 | 24 HR |
| B2B24H001:AB | | CD34 | CD2 | 24 HR |
| B2BX24H001:ABC | | CD34 | CD2 | 24 HR |
| K2B001:AB | | CD10 | CD25 | 2 HR |
| K2A001:AA | | CD10 | CD25 | 2 HR |

CHART 3

IMMUNOPHENOTYPIC CHANGES OF UNTREATED AND TREATED BLOOD OF PATIENT (8) WITH MONOCLONAL ANTIBODY TO THE HOMOLOGOUS REGION OF THE β-CHAIN OF HLA-DR ANTIGEN.

| WITH | WITHOUT | FL1 | FL2 | TIME |
|---|---|---|---|---|
|  | AN001 | CD45 | CD14 | 2 HR |
| A2001 |  | CD45 | CD14 | 2 HR |
|  | CN001 | CD3 | CD19 | 2 HR |
| C2001 |  | CD3 | CD19 | 2 HR |
|  | DN001 | CD4 | CD8 | 2 HR |
| D2001 |  | CD4 | CD8 | 2 HR |
|  | EN001 | CD3 | DR | 2 HR |
| E2001 |  | CD3 | DR | 2 HR |
|  | FN001 | CD3 | CD56&16 | 2 HR |
| F2001 |  | CD3 | CD56&16 | 2 HR |
|  | GN001 | CD28 | CD8 | 2 HR |
| G2001 |  | CD28 | CD8 | 2 HR |
|  | HN001 | CD7 | CD5 | 2 HR |
| H2001 |  | CD7 | CD5 | 2 HR |
|  | IN001 | CD13 | CD20 | 2 HR |
| I2001 |  | CD13 | CD20 | 2 HR |
|  | JN001 | CD45RA | CD25 | 2 HR |
| J2001 |  | CD45RA | CD25 | 2 HR |
|  | KN001 | CD57 | CD23 | 2 HR |
| K2001 |  | CD57 | CD23 | 2 HR |

CHART 4

IIMMUNOPHENOTYPIC CHANGES OF UNTREATED AND TREATED BLOOD SAMPLE OF PATIENT (10) WITH MONOCLONAL ANTIBODY TO THE HOMOLOGOUS REGION OF THE β-CHAIN OF HLA-DR ANTIGEN AND MONOCLONAL ANTIBODY TO THE HOMOLOGOUS REGION OF CLASS I ANTIGENS.

| WITH | WITHOUT | FL1 | FL2 | TIME |
|---|---|---|---|---|
|  | CLL0001 | CD45 | CD14 | 2 HR |
| CLL1001 |  | CD45 | CD14 | 2 HR |
| CLL2001 |  | CD45 | CD14 | 2 HR |
|  | CLL0003 | CD3 | CD19 | 2 HR |
|  |  | CD3 | CD19 | 2 HR |
| CLL1003 |  | CD3 | CD19 | 2 HR |
| CLL2003 |  | CD3 | CD19 | 2 HR |
|  | CLL0004 | CD4 | CD8 | 2 HR |
| CLL1004 |  | CD4 | CD8 | 2 HR |
| CLL2004 |  | CD4 | CD8 | 2 HR |
|  | CLL005 | CD3 | DR | 2 HR |
| CLL1005 |  | CD3 | DR | 2 HR |
| CLL2005 |  | CD3 | DR | 2 HR |
|  | CLL0006 | CD3 | CD56&16 | 2 HR |
| CLL1006 |  | CD3 | CD56&16 | 2 HR |
| CLL2006 |  | CD3 | CD56&16 | 2 HR |

The invention claimed is:

1. A method of increasing the relative number of CD45 low cells in an untreated starting cell population, wherein the starting cell population comprises a CD45 low cell sub-population and a CD45 high sub-population, and wherein the cells of the CD45 low sub-population have a lower relative density of CD45 antigen on their cell surface as compared to the cells of the CD45 high sub-population, and wherein the starting cell population includes committed hemopoietic cells comprising CD45 antigen, which method comprises:
   (i) determining that the starting cell population comprises a CD45 low cell sub-population and a CD45 high sub-population
   (ii) contacting the starting cell population with an agent selected from the group consisting of an antibody to the alpha chain of the MHC class I antigen, an antibody to the beta chain of the MHC class I antigen, an antibody to the alpha chain of the MHC class II antigen, and an antibody to the beta chain of the MHC class II antigen and
   (iii) incubating the starting cell population with the agent, whereby as a result of the contacting, a treated cell population is produced, in which the number of CD45 low cells is increased relative to the number of CD45 high cells.

2. The method according to claim 1 wherein said incubating is from 2 to 24 hours.

3. The method according to claim 1 wherein the committed hemopoietic cells are non-cancer cells.

4. The method according to claim 1 wherein the committed hemopoietic cells are differentiated cells.

5. The method according to claim 1, wherein the committed hemopoietic cells are human leukocytes, wherein the human leukocytes are found in peripheral blood, thymus spleen or tonsil tissue, and wherein the leukocytes are selected from the group consisting of lymphocytes, monocytes, polymorphonuclear cells, eosinophils and basophills.

6. A method according to claim 1 wherein said MHC class I antigen is a Human-Leukocyte-Associated (HLA)-A receptor, an HLA-B receptor, an HLA-C receptor, an HLA-E receptor, an HLA-F receptor or an HLA-G receptor and said class II antigen is an HLA-DM receptor, an HLA-DP receptor, an HLA-DQ receptor or an HLA-DR receptor.

7. The method according to claim 6 wherein the MHC class II antigen is an HLA-DR receptor.

8. A method according to claim 1 wherein the agent is a monoclonal antibody.

9. The method according to claim 8 wherein the antibody is selected from the group consisting of monoclonal antibody CR3/43 and monoclonal antibody TAL 1B5.

10. The method according to claim 1 wherein the agent is used in conjunction with an alkylating agent.

11. A method according to claim 10 wherein the alkylating agent is or comprises cyclophosphoamide.

12. The method according to claim 1, wherein the committed hemopoietic cells are leukocyte progenitors found in bone marrow.

13. The method according to claim 1 wherein the step of determining that the starting cell population comprises a CD45 low cell sub-population and a CD45 high sub-population is performed using flow cytometry.

14. The method according to claim 1 wherein the relative increase in the number of CD45 low cells in the treated cell population, as compared the number of CD45 high cells in the treated cell population, is determined using flow cytometry.

* * * * *